US011253558B2

(12) United States Patent
Chumakov et al.

(10) Patent No.: US 11,253,558 B2
(45) Date of Patent: Feb. 22, 2022

(54) OPTIMIZED ONCOLYTIC VIRUSES AND USES THEREOF

(71) Applicant: Sator Therapeutics LLC, Cleveland, OH (US)

(72) Inventors: Peter M. Chumakov, Solon, OH (US); Anastasia V. Lipatova, Moscow (RU); Stepan P. Chumakov, Moscow (RU); Natalia D. Tararova, Gates Mills, OH (US); Stephen A. Charles, Chagrin Falls, OH (US); Anton A. Komar, Gates Mills, OH (US)

( * ) Notice: Subject to any disclaimer, the term of this patent is extended or adjusted under 35 U.S.C. 154(b) by 0 days.

(21) Appl. No.: 15/716,974

(22) Filed: Sep. 27, 2017

(65) Prior Publication Data

US 2018/0085411 A1 Mar. 29, 2018

Related U.S. Application Data

(60) Provisional application No. 62/426,724, filed on Nov. 28, 2016, provisional application No. 62/400,310, filed on Sep. 27, 2016.

(51) Int. Cl.

| | |
|---|---|
| ***A61K 35/768*** | (2015.01) |
| ***C12N 7/00*** | (2006.01) |
| ***A61K 35/76*** | (2015.01) |
| ***C12N 15/01*** | (2006.01) |
| ***G01N 33/50*** | (2006.01) |

(52) U.S. Cl.

CPC ............ *A61K 35/768* (2013.01); *A61K 35/76* (2013.01); *C12N 7/00* (2013.01); *C12N 15/01* (2013.01); *G01N 33/5011* (2013.01); *C12N 2770/32321* (2013.01); *C12N 2770/32332* (2013.01); *C12N 2770/32351* (2013.01); *G01N 2333/085* (2013.01); *Y02A 50/30* (2018.01)

(58) Field of Classification Search

None

See application file for complete search history.

(56) References Cited

U.S. PATENT DOCUMENTS

2017/0056458 A1* 3/2017 Champion ............ C07K 14/56

OTHER PUBLICATIONS

Matveeva et al. (Acta Naturae, Apr.-Jun. 2015, vol. 7, p. 6-16).*

Matveeva etal (Molecular Therapy, 2015, p. 1-14).*

Chumakov et al. (Molecular Biology, 2012, p. 639-650).*

Le Boeuf F et al, Synergistic interaction between oncolytic viruses augments tumor killing, Molecular Therapy, pp. 888-895, May 1, 2010, vol. 18, No. 5, Nature Publishing Group, GB.

J.R. Tysome et al, A Novel Therapeutic Regimen to Eradicate Established Solid Tumors with an Effective Induction of Tumor-Specific Immunity, pp. 6679-6689, Oct. 22, 2012, vol. 18, No. 24, Clinical Cancer Research, US.

Estanislao Nistal-Villan et al, Enhanced therapeutic effect using sequential administration of antigenically distinct oncolytic viruses expressing oncostatin M in a Syrian hamster orthotopic pancreatic cancer model, Dec. 1, 2015, vol. 14, No. 1, Molecular Cancer, XP0554321208.

Howard L. Kaufman et al, Oncolytic viruses: a new class of immunotherapy drugs, pp. 642-662, Sep. 1, 2015, vol. 14, No. 9, Nature Reviews. Drug Discovery, GB.

International Search Report for PCT Application No. PCT/US2017/053659 dated Feb. 8, 2018.

Muhannad Alkassar et al: "The combined effects of oncolytic reovirus plus Newcastle disease virus and reovirus plus parvovirus on U87 and U373 cells inA vitro and inA vivo", Journal of Neuro-Oncology, Kluwer Academic Publishers, BO, vol. 104, No. 3, May 24, 2011 (May 24, 2011), pp. 715-727.

Suskind R G et al: "Viral agents oncolytic for human tumors in heterologous host; oncolytic effect of Coxsackie B viruses", Proceedings of the Society for Experimental Biology and Medicine, Sage Publications Ltd, GB, vol. 94, No. 2, Feb. 1, 1957, pp. 309-318.

Demina et al: "Non-Pathogenic Enteroviruses Possessing Potential Oncolytic Properties", Jan. 1, 2014, pp. 62-64.

Stina Israelsson et al: "Cytolytic replication of echoviruses in colon cancer cell lines", Virology Journal, Biomed Central, London, GB, vol. 8, No. 1, Oct. 14, 2011, p. 473.

Keith A. Lawson & Don G. Morris, Oncolytic virotherapy for renal cell carcinoma: a novel treatment paradigm?, Expert Opinion on Biological Therapy, 12:7, 891-903.

* cited by examiner

*Primary Examiner* — Agnieszka Boesen

(74) *Attorney, Agent, or Firm* — Fay Sharpe LLP

(57) ABSTRACT

Methods of inhibiting or reducing tumor growth are disclosed. A composition containing at least one selected oncolytic virus is administered within a tumor of a patient. The virus kills cancerous cells and induces a systemic and lasting anti-tumor immunity that is also compatible with other cancer treatments. Also disclosed are methods of creating synthetic viruses for targeting cancerous tumors.

16 Claims, 9 Drawing Sheets
(8 of 9 Drawing Sheet(s) Filed in Color)

Specification includes a Sequence Listing.

MRI post viral therapy

MRI post resection

OPTIMIZED ONCOLYTIC VIRUSES AND USES THEREOF

CROSS-REFERENCE TO RELATED APPLICATIONS

This application claims priority to U.S. Provisional Patent Application Ser. No. 62/400,310, filed Sep. 27, 2016, and to U.S. Provisional Patent Application Ser. No. 62/426,724, filed Nov. 28, 2016. The disclosures of these applications are incorporated by reference in their entirety.

BACKGROUND

This application incorporates by reference a sequence listing submitted herewith as SATO2000002_ST25.txt, created on Sep. 26, 2016, and having a file size of 17,720 bytes.

The present disclosure relates to methods for inhibiting or reducing cancerous cells proliferation and malignant tumor progression. Compositions for use in such methods are also disclosed. Finally, methods for preparing various types of bioselected and synthetic viruses for use in treating cancerous tumors are also described herein.

Cancer is the abnormal growth of cells, which can create masses of tissue that can become malignant tumors or neoplasms. These formations can invade and destroy surrounding tissues, and may spread to other parts of the body forming metastases.

Cancer cells are, in general, susceptible to infection and mortality by viruses of many families. This may be due to: (i) better exposure of malignant cells to viruses due to the disordered tissue architecture, loss of cell-to-cell contacts, and leaky neovasculature; (ii) frequent over-expression of many cell-surface proteins used by viruses as cell-entry receptors; and (iii) more favorable conditions for virus replication inside cancer cells due to the frequent loss of antiviral innate immunity mechanisms, compromised cell death pathways, and pre-activated nucleic acids and protein synthesis.

It would be advantageous to develop additional viruses and methods of using such viruses, including simultaneous applications of several different oncolytic viruses and different combinations of these viruses, to provide personalized treatment and to prevent relapses and incomplete cure of disease due to the resistance of cancerous cells to some viruses and the development of antiviral adaptive immunity in patients in need thereof.

BRIEF DESCRIPTION

Disclosed in various embodiments herein are methods for a selective killing of cancerous cells and a systemic elimination of tumor metastases by the administration of a panel of oncolytic viruses. Different combinations of oncolytic viruses can be administered to a patient either simultaneously (i.e. multiple viruses in a single administration) or sequentially (i.e. one virus administered at a time, but multiple viruses given over multiple administrations over time). The combinatorial use of oncolytic viruses can improve therapeutic outcomes. Bioselected and synthetic viruses and methods for creating such viruses are also described. Methods for determining a patient's sensitivity to an oncolytic virus are also disclosed.

Disclosed in various embodiments are methods of treating a cancer patient, comprising: administering to the patient a first composition containing an effective amount of at least a first oncolytic virus for a first time period; and administering to the patent a second composition containing an effective amount of at least a second oncolytic virus that is different from the first oncolytic virus for a second time period.

The second composition can be administered between 24 hours to 24 weeks after the first composition is administered. In more specific embodiments, the second composition is administered between one week to six weeks after the first composition is administered.

The first composition can be administered multiple times during the first time period. The second composition can be administered multiple times during the first time period The first and second compositions containing different viruses that are not cross-neutralized by antiviral antibodies can be administered orally, nasally, intravenously, intra-arterially, intradermally, subcutaneously, intramuscularly, intraperitoneally, intrapleurally, intraurethrally, intravaginally, intratumorally, intracranially, intraspinally, or by a systemic administration of a cell carrier (isolated from a patient) pre-infected with the virus in vitro.

The first and second (or third, etc) oncolytic viruses may each be present in their respective compositions in a dosage from about $10^4$ (10^4) TCID50/mL to $10^{11}$ (10^11) TCID50/mL.

The first and second (or third, etc) oncolytic viruses used in these treatment methods generally differ in their host-cell surface receptor required for cell entry, or differ in other cancer cell specific or tumor environment specified variations affecting efficient replication or cancer cell killing. The host-cell surface receptors required for cell entry include, but are not limited to, PVR (CD155), integrin $\alpha2\beta1$, integrin $\alpha V\beta3$, integrin $\alpha V\beta6$, ICAM-1, CD55, CXADR, CD46, JAM-1, PVRL1, PVRL4, SLAM (CD150), PSLG1 (CD162), SCARB2, DC-SIGN, L-SIGN, VLDVR, NRAMP2, heparin sulphate or sialic acid. The cancer cell specific or tumor environment specified variations affecting efficient replication or cancer cell killing include, but are not limited to, specific oncogenic mutations (in K-Ras, H-Ras, N-Ras, EGFR, p53, HER2 genes and other); specific alterations in cell proliferation or cell death mechanisms; deficiencies in components of the interferon induction pathways; deficiencies in components of the interferon response pathways; changes in activities of membrane-bound and secreted proteases, protease inhibitors, or components of extracellular matrix; development of stroma and neovascular network within the tumor; and tumor infiltrations with macrophages, leukocytes, dendritic cells, etc.

In particular embodiments, the first and second compositions each contain a plurality of oncolytic viruses. The first oncolytic virus and the second oncolytic virus can be independently selected from, but is not limited to, a human enterovirus (such as an echovirus, a Coxsackievirus, a Sabin strain of poliovirus, or a rhinovirus); a reovirus (such as type 1, type 2 and type 3 mammalian orthoreoviruses, or other); a paramyxovirus (such as human measles or mumps viruses, canine distemper virus, mouse Sendai virus, or avian Newcastle disease virus); a rhabdovirus (such as vesicular stomatitis virus, Carajas virus, Maraba virus, or Piry virus); a togavirus; a Herpes family virus; an adenovirus; a poxvirus; and a hybrid virus containing natural or modified components derived from other viruses within or outside a particular virus family. Combinations of these viruses being administered simultaneously are also contemplated herein. The first and second compositions can have, in various embodiments, a total of two or three or four different viruses. As desired, additional compositions can be administered sequentially to the patient as well at different intervals.

Also disclosed are methods of generating an optimized oncolytic virus, comprising: (i) culturing a first oncolytic virus on a first cell culture in the presence of a synthetic ribonucleoside or ribonucleotide analog to create mutagenized viruses; and (ii) culturing the mutagenized viruses on a second cell culture using serial dilution to identify the optimized oncolytic virus.

The synthetic ribonucleoside or ribonucleotide analog may be ribavirin; 5-azacytidine; 5-fluorouracil; 5-Aza-5,6-dihydro-2-deoxycytidine; N4-aminocytidine; N1-methyl-N4-aminocytidine; 3,N4-ethenocytidine; 3-methylcytidine; 5-hydroxycytidine; N4-dimethylcytidine; 5-(2-hydroxyethyl)-cytidine; 5-chlorocytidine; 5-bromocytidine; N4-methyl-N4-aminocytidine; 5-aminocytidine; 5-nitrosocytidine; 5-(hydroxyalkyl)-cytidine; 5-(thioalkyl)-cytidine and cytidine glycol; 5-hydroxyuridine; 3-hydroxyethyluridine; 3-methyluridine; O2-methyluridine; O2-ethyluridine; 5-aminouridine; O4-methyluridine; O4-ethyluridine; O4-isobutyluridine; O4-alkyluridine; 5-nitrosouridine; 5-(hydroxyalkyl)-uridine; 5-(thioalkyl)-uridine; 1,N6-ethenoadenosine; 3-methyladenosine; N6-methyladenosine; 8-hydroxyguanosine; O6-methylguanosine; O6-ethylguanosine; O6-isopropylguanosine; 3,N2-ethenoguanosine; O6-alkylguanosine; 8-oxo-guanosine; 2,N3-ethenoguanosine; or 8-aminoguanosine. The synthetic ribonucleoside or ribonucleotide analog may be present with the first cell culture in an amount of about 0.1 mM to about 0.5 mM.

In specific embodiments, the second cell culture is different from the first cell culture, and contains cells that are the desired target of the optimized oncolytic virus. This confirms that the optimized oncolytic virus replicates well within the cancerous cells that are to be treated.

The mutagenized viruses can be collected from the first cell culture after a first time period of about 12 hours to about 36 hours. The first oncolytic virus can be added to the first cell culture in an amount of about 0.05 PFU/cell to about 0.50 PFU/cell.

In some embodiments, the first oncolytic virus is also cultured on the first cell culture in the presence of antibodies, such that the optimized oncolytic virus has increased resistance to the antibodies.

Steps (i) and (ii) are generally repeated sequentially, with the optimized oncolytic virus of step (ii) being used as the first oncolytic virus of step (i) for each subsequent repetition. Each additional repetition leads to additional mutagenized virus derived from the fittest virus of the prior round, and additional selection for the desired traits/properties. This can be used to both select for viruses that can replicate in a particular target cell type, and to select for viruses that antibodies have less effect against.

Also disclosed are methods of generating a synthetic targeted virus from a reference virus, comprising: for each codon in the reference virus that codes for a given amino acid, identifying all codons that code for the given amino acid, and using in the synthetic targeted virus the codon for the given amino acid that (i) has the most similar frequency of usage in the ORFeome (entire sets of protein-encoding open reading frames (ORFs) expressed) of the cancer cells in comparison with the reference virus ORFeome and/or (ii) would be the most optimal in terms of its frequency/decoding rate to ensure that the local translation kinetics (given the repertoire of tRNAs present in non-transformed and malignant cells) of the viral mRNA in the cancer cells are similar to that of the virus translation kinetics in the non-transformed cells. This takes advantage of the fact that (i) the abundance of tRNAs is usually directly proportional to the frequency of codon usage in a given cell/tissue; (ii) frequently used codons are, as a rule, translated more rapidly than infrequently used ones (and vice versa) due to the more ready availability (during decoding of the message) of corresponding frequent cognate tRNAs; (iii) optimal/frequent and nonoptimal/rare codons differ among cell types/tissues coordinated with changes in the population of tRNA genes; (iv) selected tRNAs that are induced and expressed at high levels in proliferating (i.e. cancerous) cells (these tRNAs were shown to drive cancer cell progression) are typically repressed and expressed at low levels in differentiating (i.e. non-cancerous) cells; (v) synonymous codon usage not only affects mRNA translation rates/protein expression levels, but also affects protein folding in the cell; and (vi) codon usage profile serves as a kinetic guide for protein folding in the cell. The expression of protein from the synthetic virus is thus attenuated in normal cells, but enhanced in cancerous cells, while preserving correct folding of the viral proteins in cancer cells, but simultaneously affecting the folding in normal cells.

In particular embodiments, the reference virus is an oncolytic virus. The synthetic targeted virus may have less than 85% nucleotide identity with the reference virus, or may have less than 80% nucleotide identity, or less than 75% nucleotide identity. Generally, however, the synthetic targeted virus has at least 67% nucleotide identity with the reference virus.

Also disclosed are methods for identifying a patient's sensitivity to an oncolytic virus, comprising: infecting tumor cells obtained from the patient with a first oncolytic virus; culturing the infected tumor cells to determine a concentration of the first oncolytic virus; and identifying the patient as being sensitive to the first oncolytic virus if the concentration is greater than a threshold value.

The threshold value may vary depending on the virus being tested. In some particular embodiments, the threshold value may be $10^6$ (10^6) TCID50 per mL. The tumor cells can be collected from the patient by either surgery or biopsy.

The tumor cells may be suspended in a cell culture medium prior to being infected. The infected tumor cells can be cultured by incubation at a temperature from about 35° C. to about 45° C. in an atmosphere containing about 5% $CO_2$ for a period of about 24 hours to about 72 hours.

The oncolytic virus may be a human enterovirus; a reovirus; a paramyxovirus; a rhabdovirus; a togavirus; a Herpes virus; a parvovirus; an adenovirus; a poxvirus; or a hybrid virus containing natural or modified components derived from other viruses within or outside a particular virus family.

The cancerous tumors treated by these methods and compositions and viruses disclosed herein can include breast, cervical, colon, liver, lung, ovarian, pancreatic, prostate, renal, adrenal, thyroid, brain, soft tissue, mesothelial, blood or bone cancer tumors.

The oncolytic virus compositions described herein can be administered in combination with chemotherapy, immunotherapy, radiation therapy, drug therapy, or cell transplantation.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIG. 1A shows the tumor volume ($mm^3$) over time (days) for C33A cell line alone (squares) or infected with Coxsackievirus B3 (Cox-B3, circles) or Coxsackievirus A7 (Cox-A7, triangles). The y-axis runs from 0 to 3000 in intervals of 500. The x-axis runs from 0 to 50 in intervals of 10. At day 50, the C33A has the largest tumor volume, followed by Cox-B3 and then Cox-A7.

FIG. 1B shows the tumor volume ($mm^3$) over time (days) for AsPC1 cell line alone (squares) or infected with Coxsackievirus B4 (Cox-B4, circles) or Coxsackievirus A7 (Cox-A7, triangles). The y-axis runs from 0 to 3000 in intervals of 500. The x-axis runs from 0 to 50 in intervals of 10. At day 50, the AsPC1 has the largest tumor volume, followed by Cox-A7 and then Cox-B4.

FIG. 1C shows the tumor volume ($mm^3$) over time (days) for MCF7 cell line alone (squares) or infected with Coxsackievirus B6 (Cox-B3, circles) or Echovirus 1 (Echo1, triangles). The y-axis runs from 0 to 3000 in intervals of 500. The x-axis runs from 0 to 50 in intervals of 10. At day 50, the MCF7 has the largest tumor volume, followed by Cox-B6 and then Echo1.

DETAILED DESCRIPTION

Figure 1A:
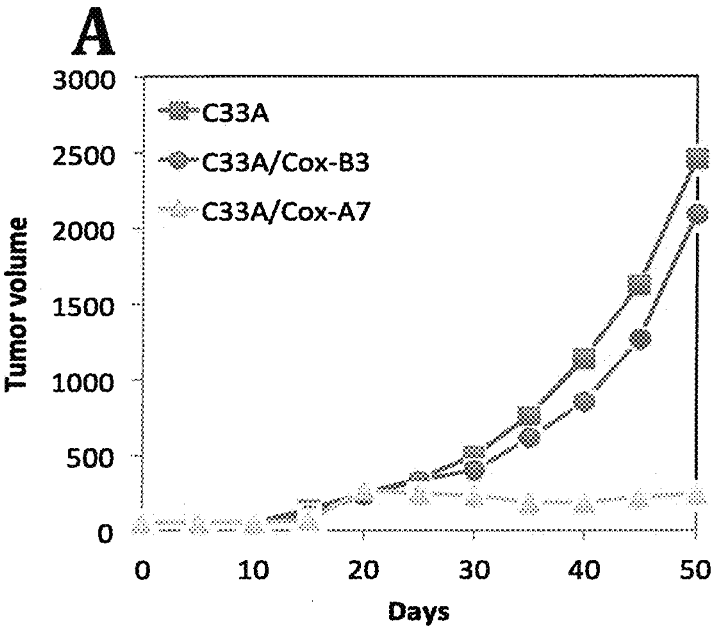
FIGS. 1A-1C are a set of graphs indicating tumor growth over a period of 50 days in nude mice with xenografts of C33A, AsPC1, and MCF7 human carcinoma cell lines.

The present disclosure may be understood more readily by reference to the following detailed description of desired embodiments and the examples included therein. In the following specification and the claims which follow, reference will be made to a number of terms, which will be defined to have the following meanings.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "tumor" is used herein to refer both to a neoplasm that has formed a lump and to a neoplasm that has not formed a lump. The tumor can be malignant, or potentially malignant, or a secondary tumor.

The term "oncolytic virus" refers to a virus having oncolytic properties. The oncolytic virus may be natural, improved by selection, or synthetically created.

The term "CV1" refers to a cell line derived from African green monkey kidneys (ATCC No. CCL-70). CV-1 cells exhibit fibroblast-like morphology, grow adherently to glass or plastic surfaces, and are negative for reverse transcriptase.

The term "TCID50" refers to 50% tissue culture infective dose, which is a measure of infectious virus titer. This endpoint dilution assay quantifies the amount of virus required to kill 50% of infected hosts or to produce a cytopathic effect in 50% of inoculated tissue culture cells.

The term "PFU" refers to plaque forming units in a virus sample, which is one measure of virus quantity. This assay is based on a microbiological method conducted in petri dishes or multi-well plates. Specifically, a confluent monolayer of host cells is infected with the virus at varying dilutions and covered with a semi-solid medium to prevent the virus infection from spreading indiscriminately. A viral plaque is formed when a virus infects a cell within the fixed cell monolayer. The virus-infected cell will lyse and spread the infection to adjacent cells where the infection-to-lysis cycle is repeated. The infected cell area will create a plaque (an area of infection surrounded by uninfected cells), which can be seen visually or with an optical microscope. Plaques are generally counted manually and the results, in combination with the dilution factor used to prepare the plate, are used to calculate the number of plaque forming units per sample unit volume (PFU/cell). The PFU/cell result represents the number of infective particles within the sample and is based on the assumption that each plaque formed is representative of one infective virus particle.

The term "identity" refers to the degree to which a pair of sequences (nucleotide or amino acid) has the same residue in the same location. Identity is measured by dividing the number of identical residues by the total number of residues (gaps are not counted) and multiplying the product by 100 to achieve a percentage. Thus, two copies of exactly the same sequence have 100% identity, but sequences that have deletions, additions, or substitutions may have a lower degree of identity. Those skilled in the art will recognize that several computer programs, such as those that employ algorithms such as BLAST, are available for determining sequence identity. BLAST nucleotide searches are performed with the NBLAST program, and BLAST protein searches are performed with the BLASTP program, using the default parameters of the respective programs.

The present disclosure relates to methods for increasing the probability of positive therapeutic responses and overcoming the problem of development of antiviral immunity through the combinational use of a panel of oncolytic viruses that differ in antigenic structure and requirements for host-cell specific functions affecting virus entry and replication.

In this regard, oncolytic viruses act by a dual mechanism involving a direct killing of cancer cells during their lytic infection, and the induction of systemic anti-tumor immunity that provides a long-lasting therapeutic effect even after clearing of the virus. Unlike chemotherapeutic drugs that have limited efficacy against the recurrent growth of tumors due to the resistance of cancer initiating stem cells, many oncolytic viruses are capable of infecting and killing cancer stem cells, thereby limiting probability of relapses. It is also noted that while normal cells display viral interference (a cell infected with a first virus display reduced susceptibility to being infected by a second virus), cancer cells may not. Due to distinct mechanisms of action, oncolytic viruses could complement conventional chemotherapy approaches, especially in cases of therapy-associated resistance to other drugs.

Many different virus families could be used for the development of safe and potent oncolytic virus strains. Among these are (1) naturally occurring animal viruses that have no, or very limited, pathogenicity in humans, (2) attenuated strains of human viruses commonly used as live preventative vaccines, (3) some isolates of human viruses with no or limited pathogenicity, and (4) engineered or bio-selected viruses with increased tumor selectivity due to (a) the elimination of certain viral functions required for the virus to kill in normal cells, or (b) providing additional modalities for the entry into, or specific killing of, cancerous cells.

Clinical studies involving many different types of oncolytic viruses indicate that oncolytic virus therapy in general is safe and is associated with minimal adverse effects that include mild flu-like symptoms lasting up to 24 hours, fever, chills, fatigue, headache, nausea, hypotension, tachycardia, hypertension, anorexia, and myalgia. However, the therapeutic efficiency of viral oncolysis is not predictable. In spite of some remarkable therapeutic effects in some patients, randomized clinical trials commonly reveal rather modest responses. Many issues still need to be addressed to make oncolytic viruses competitive and efficient cures for cancer. Among these are the need for reliable oncolytic virus delivery protocols, improved virus spreading within the tumor, overcoming immunosuppressive effects of the tumor microenvironment, management of dangers related to rapid lysis of the tumor and hyperactive innate immunity responses, etc.

One major obstacle to oncolytic virus therapy is the remarkable individual variability of cancer cells between patients, which requires personalized approaches. Virtually every case of cancer is unique in terms of the combinations of genetic defects. Therapeutic responses to a particular oncolytic virus strain depend on a number of personalized parameters of the patient's tumor. In particular, cancer cells may be deficient in recognizing certain viruses, but retain the ability to sense and contain other types of viruses. Cancer cells may differ in certain features that relate to cell death, cell-cycle control, and metabolic transformation, which are important to some viruses but are obsolete for others. Moreover, as cancer cells are genetically unstable, certain host-cell factors required for virus infection and replication may be lost during the course of oncolytic virus therapy, thereby permitting relapses from the proliferation of the therapy-resistant population of cancer cells. As a result, the response of an individual tumor to a particular virus is difficult to predict.

Another obstacle to oncolytic virus therapy is the unavoidable development of adaptive immunity against the therapeutic virus strain. Neutralizing antibodies destroy the virus during its journey to sensitive cancer cells, thereby lowering the probability of infection. Higher doses of the virus could overcome this resistance at certain stages of treatment, although the efficiency of infection decreases during the treatment course. However, the use of a single oncolytic virus for an extended period is especially prone to relapse due to either (1) selection of cells resistant to the virus or (2) the induction of neutralizing antibodies. Although various combination therapy regimens with cytotoxic and immunosuppressive drugs are being tested to improve outcomes, there are still challenges of the complex therapeutic trade-offs related to the conflicting mechanisms of action.

The present disclosure relates to methods for using non-pathogenic human viruses with oncolytic activity to treat cancer patients, and to panels of combinations of different oncolytic viruses. The viruses used in combination together should differ in their antigenic structures, so that they do not cross-neutralize with antibodies. The viruses can display overlapping requirements for host-cell specific factors, but should not be identical. These requirements may include but are not limited to, the host-cell surface receptor used for virus-entry receptors, components of the antiviral innate immune system, etc. The viruses can be used sequentially or simultaneously, in combination of two, three or more different viruses. Examples of oncolytic virus combinations for sequential and simultaneous applications are disclosed.

Further disclosed are methods for making or selecting new oncolytic viruses that are more optimized (relative to their natural counterparts) to increase the antigenic and functional diversity of the therapeutic panels described herein for cancer treatment using viruses. Such synthetic viruses can be made using codon optimization strategies that induce propagation in the selected cancer cells/tissues (and cause enhanced killing of them) while possessing attenuated expression in normal cells/tissues.

In one broad aspect, the present disclosure relates to methods for treating cancer patients using oncolytic viruses. Generally, a first composition containing an effective amount of at least a first oncolytic virus is administered to the patient for a first time period. Then, a second composition containing an effective amount of at least a second oncolytic virus is administered to the patient for a second time period. The compositions are administered sequentially. In other words, the first composition is administered, then the administration of the first composition is stopped and the second composition is administered. Put another way, a panel of oncolytic virus compositions is administered sequentially to the patient, i.e. one composition at a time but multiple compositions in a row.

In this regard, different strains of virus serotypes rely on different host-cell surface protein receptors to gain entry to cells. For example, Echovirus 1 relies on integrin $\alpha 2\beta 1$ (alpha-2-beta-1); Echoviruses 7, 12, and 21 on CD55 (also known as DAF); Coxsackieviruses A7 and A9 on Integrin $\alpha V\beta 3$, Integrin $\alpha V\beta 6$, ICAM-1, and CD55; Coxsackieviruses B1-B6 on CXADR (also known as Coxsackievirus and adenovirus receptor or CAR); Coxsackieviruses B1, B3 and B5 on CD55; Edmonston strains of measles virus rely on CD46; canine distemper virus relies on nectin 4; and orthoreoviruses rely on JAM-1. It is contemplated that one method by which cancer cells resist infection by viruses is by changing the expression and cell-surface exposure of receptors. There may be other factors that affect the efficiency of a virus to infect a particular cell type. As a result, the use of sequential viruses should allow for more extended courses of virotherapy, avoiding diminished efficiency of a single oncolytic virus strain because of the development of neutralizing antibodies against a particular virus or selection of cancer cells that are resistant to the particular virus (e.g. by changing the expression of the host-cell surface receptor needed by the particular virus).

Thus, the first and second oncolytic viruses should be different from each other, for example in the host-cell surface receptor required for cell entry. More specifically, the host-cell surface receptor required for cell entry oncolytic viruses can be selected from PVR (CD155), integrin $\alpha 2\beta 1$ (alpha-2-beta-1), integrin $\alpha V\beta 3$ (alpha-V-beta-3), integrin $\alpha V\beta 6$ (alpha-V-beta-6), ICAM-1, CD55 (aka DAF), CXADR (aka CAR), CD46, JAM-1, PVRL1, PVRL4, SLAM (CD150), L-SIGN, VLDVR, NRAMP2, sialic acid, PGSL-1 (aka CD162), SCARB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparan sulfate. The first and second oncolytic viruses could also be different from each other by targeting different specific defects in a particular type of cancer cells, such as mutations within proto-oncogenes, or different tumor suppressor genes, or different changes in programmed cell death pathways, alterations within various components of antiviral innate immunity mechanisms responsible for pathogens sensing and the development of antiviral resistance in response to interferon, etc. These defects in cancer cells may confer selective replication and cell killing advantages to some viruses, while being obsolete to others.

The sequential application of different oncolytic viruses increases incidence of positive therapeutic responses among patients. However, as some of the virus strains in the panel may not be active against malignant cells of the patient, sequential application may result in a waste of time applying those ineffective virus strains. As an alternative, the simultaneous use of several oncolytic virus strains can be considered. Put another way, the first composition and/or the second composition can comprise a plurality of different oncolytic viruses. Two to four different oncolytic virus strains may be present in each oncolytic composition of the panel. The virus strains in each composition should be chosen based on their complementing spectrums toward different types of malignant cells. The approach has the following advantages and benefits for the patient: (i) better chances for positive match of an active oncolytic virus capable of destroying the patient's tumor; (ii) lower probability of selection of tumor cells that are resistant to a particular virus that uses a specific mechanism of cell entry and replication; and (iii) lower probability of complications because of an individual sensitivity of the patient to an oncolytic virus. Viruses in the oncolytic compositions should induce the production of interferons that protect the patient from potential virus pathogens. Cancer cells are generally less sensitive to interferon, which underlies the specificity of oncolytic virus action against malignant cells. The use of mixtures of viruses would also permit the use of (a) conditionally pathogenic viruses or (b) custom-selected variants of oncolytic viruses that have not undergone extensive safety trials. The latter is particularly important for personalized approaches to oncolytic virus therapy. A conditionally (or potentially) pathogenic virus originates from rapidly evolving non-pathogenic strains that form heterogeneous quasi-species, some variations of which may acquire pathogenic properties, especially in immunocompromized individuals.

The compositions containing the oncolytic viruses can be used/administered sequentially after a time interval. In particular embodiments, the interval for which a given composition is used is between about 24 hours to about 24 weeks. In other embodiments, the interval is between about one week and about six weeks. In other words, the second composition is administered after the first composition is administered for this time period. It is noted that the compositions can be administered multiple times during this time period, as well as in multiple locations on the patient's body.

The oncolytic viruses used in the methods and compositions disclosed herein can be of the family of Picornaviridae, Reoviridae, Paramyxoviridae, Togaviridae, Rhabdoviridae, Adenoviridae, Herpesviridae, Parvoviridae, Poxviridae. In particular embodiments, the oncolytic viruses can be independently selected from a human echovirus; Coxsackievirus; a Sabin strain of poliovirus; human reovirus type 1, 2, or 3; a measles virus; a mumps virus; a Newcastle disease virus; a Sendai virus; a Vaccinia virus; a canine distemper virus; Maraba virus; or vesicular stomatitis virus (VSV).

Specific viruses contemplated for use include echoviruses 1-7, 9, 11-27, 29-33; Coxsackieviruses A1-A22 and A24; Coxsackieviruses B1-B6; poliovirus Sabin strains 1-3; measles virus vaccine strains Edmonston, Moraten, Zagreb, AIK-C, Rubeovax, Schwarz, CAM-70, Changchun-47, Leningrad-4 and Shanghai-191; mumps virus vaccine strains Jeryl-Lynn, RIT 4385, Leningrad-3, Leningrad-Zagreb, Urabe Am9, and S79; Newcastle disease virus strains La Sota, B1, V4, VG-GA, Ulster 2C, Fuller, R2B, Mukteswar, and Komarov; Sendai virus strains Cantell, Fushimi, Z, and Hamamatsu; Vaccinia virus strains Lister, Dryvax, EM63, ACAM2000, Ankara, and LC16m8.

The dosage of each virus in the oncolytic compositions is from about $1\times10^{4}$ (10^4) TCID50 per milliliter (mL) to about $1\times10^{11}$ (10^11) TCID50 per milliliter.

As one example, the following oncolytic virus panel can be administered sequentially:

Reovirus type 1 (uses sialic acids for cell entry);

Coxsackievirus B5 (requires CD55);

Echovirus type 1 (requires integrin $\alpha2\beta1$ for cell entry);

Coxsackievirus A7 (requires Integrins $\alpha V\beta3$ and $\alpha V\beta6$, ICAM-1 and CD55);

Measles virus, Edmonston (requires CD46);

Coxsackievirus B6 (requires CXADR and CD55);

Sabin poliovirus type 1 vaccine strain (uses CD155 as a receptor).

Natural infection with enteroviruses occurs through the gastrointestinal tract by infection of lymphoid cells. However, the intestinal route may be blocked if the individual has been previously exposed to the virus (i.e. intestinal resistance). It is contemplated that the oncolytic compositions/viruses can be administered via an intratumoral, oral, nasal, intravenous, intra-arterial, subcutaneous, intradermal, intramuscular, intraperitoneal, intrapleural, intravaginal, intraurethral, intraspinal and intracranial route, depending on the malignant disease and particular virus strains used. The compositions/viruses can also be administered by systemic administration of a cell carrior pre-infected with the composition/viruses in vitro.

It would also be advantageous to culture and obtain additional potent strains of oncolytic viruses that are capable of lysing a wider spectrum of cancer cells or that do not cross-neutralize with antibodies induced in response to previously administered oncolytic viruses. Two such methods are described herein.

First, mutagenesis may be induced in a virus using synthetic ribonucleotide or ribonucleoside analogs, which can be incorporated into viral RNA genomes by viral RNA polymerases, resulting in aberrant nucleotide base pairings during replication, thereby producing mutagenized viruses (mutated RNA species). One such ribonucleoside analog is ribavirin, although other synthetic ribonucleotide and ribonucleoside analogs selected from the group consisting of guanosine, uridine, cytidine, and adenosine analogs can be used for the purpose. Other analogs that could be used include but not limited to the antiviral drugs developed for lethal mutagenesis of viruses, such as 5-azacytidine; 5-fluorouracil; 5-Aza-5,6-dihydro-2-deoxycytidine; N4-aminocytidine; N1-methyl-N4-aminocytidine; 3, N4-ethenocytidine; 3-methylcytidine; 5-hydroxycytidine; N4-dimethylcytidine; 5-(2-hydroxyethyl)-cytidine; 5-chlorocytidine; 5-bromocytidine; N4-methyl-N4-aminocytidine; 5-aminocytidine; 5-nitrosocytidine; 5-(hydroxyalkyl)-cytidine; 5-(thioalkyl)-cytidine and cytidine glycol; 5-hydroxyuridine; 3-hydroxyethyluridine; 3-methyluridine; O2-methyluridine; O2-ethyluridine; 5-aminouridine; O4-methyluridine; O4-ethyluridine; O4-isobutyluridine; O4-alkyluridine; 5-nitrosouridine; 5-(hydroxyalkyl)-uridine; 5-(thioalkyl)-uridine; 1, N6-ethenoadenosine; 3-methyladenosine; N6-methyladenosine; 8-hydroxyguanosine; O6-methylguanosine; O6-ethylguanosine; O6-isopropylguanosine; 3,N2-ethenoguanosine; O6-alkylguanosine; 8-oxo-guanosine; 2; N3-ethenoguanosine; and 8-aminoguanosine and other derivatives. Such analogs cannot serve as a substrate for RNA synthesis by cellular RNA polymerases, but rather are used by more promiscuous RNA replicases of many viruses. The presence of these analogs in a cell culture substantially increases mutation rates of RNA viruses, thereby facilitating and accelerating the process of bioselection.

Broadly, in this first method, an oncolytic virus is propagated in a first cell culture in the presence of the synthetic ribonucleoside analog. The oncolytic virus is added in an amount of about 0.05 PFU/cell to about 0.50 PFU/cell. The synthetic ribonucleoside analog is present in an amount of about 0.02 mM to about 0.5 mM. After a first time period of about 12 hours to about 36 hours, the mutagenized virus is collected. The mutagenized virus is then propagated in a second cell culture using serial dilution. The virus of the last dilution that displays a cytopathic effect is harvested. As desired, additional rounds of mutagenesis and serial dilution could be performed, with the mutagenized virus selected by serial dilution becoming the oncolytic virus used on the first cell culture and exposed to the synthetic ribonucleoside analog in the next round of mutagenesis. It is contemplated that the first cell culture is used for mutagenesis, and the second cell culture is used for virus selection. Ideally, the second cell culture contains cells that are the desired target of the final bioselected/optimized oncolytic virus. As a result, oncolytic viruses are obtained that can replicate in the second cell culture. This is one way, for example, of modifying a virus so that it can more readily infect cell types that it previously had difficulty infecting.

The second method is similar to the first method, but the oncolytic virus is also cultured on the first cell culture in the presence of antibodies. In the second method, the first and second cell cultures can be the same cell type, as the successive rounds of mutagenesis/antibody exposure and serial dilution are intended to select for viruses that have increased resistance to the antibodies.

The present disclosure also discloses a novel approach for producing new synthetic viruses by chemical synthesis of the entire viral genome with altered synonymous codon usage aimed at enhancing viral proliferation and correct folding of viral proteins specifically in cancer cells and attenuating their proliferation (and folding of viral proteins) in normal cells.

In this regard, the viral genome (contained in the DNA or RNA of a virus) harbors all the information necessary for viral expression and replication. Virus genomes have a limited number of genes that encode for the proteins essential for viral replication and assembly of virions. Many viral genomes also contain genes encoding for proteins that suppress cellular defense mechanisms. The order and location (the beginning and the end) of individual genes in many viral genomes is well-known.

When a host cell is infected by a virus, the protein synthesis machinery of the cell synthesizes the viral proteins encoded by the viral genome. Decoding, or translation, of viral mRNA is performed by ribosomes, with aminoacyl-tRNAs adding amino acids to grow the protein chain during protein synthesis. When the viral proteins mature, became functional and reach a sufficient concentration, the virions assemble to form a new virus. The new virus egresses the host cell and is available to infect new cells.

The genetic code describes the correspondence between the sequence of a given nucleotide triplet in the mRNA (i.e. a codon) and the amino acid that is identified by that codon. The genetic code is degenerate, with up to six synonymous codons encoding for a given amino acid. However, the usage of each codon for a given amino acid is not uniform, and the frequency of codons is known as codon bias.

Synonymous codons (encoding the same amino acid) were initially presumed to have entirely equivalent functions. However, the finding that synonymous codons are not present at equal frequencies in genes/genomes suggested that codon choice might have functional implications beyond amino acid coding. The pattern of non-uniform codon use varies between organisms and between different cells/tissues expressing different sets of genes. Organism/gene and tissue specific codon choice is related to organism and tissue/cell specific differences in tRNA populations. The abundance of tRNAs is known to be directly proportional to the frequency of codon usage, and thus in a given organism and/or cell/tissue, frequently-used codons are generally translated more rapidly than infrequently-used codons, and vice versa. The rate of decoding depends on the concentration of the tRNAs surrounding the ribosomes during translation. The occurrence of synonymous codons and the abundance of their corresponding tRNAs is one of the major causes of the differential efficiency in mRNA translation.

It has also been found that synonymous codon usage affects mRNA stability and, most importantly, protein folding. Synonymous codons can modulate protein folding by tuning the kinetics of translation. In vivo, protein folding begins co-translationally as nascent peptide chains emerge from the ribosome exit tunnel. Variations in local translation rates, due to difference in tRNA abundance for a given codon, can facilitate protein folding by allowing ordered, sequential structuring of the nascent polypeptide chains emerging from the ribosome. The placement/distribution of rare codons and frequent codons along the mRNA can actively guide protein folding in the cell. Thus, synonymous codon usage regulates not only translation elongation, but also co-translational folding, and protein quality in the cell. It is thus possible to modulate both protein expression levels and protein structural properties by changing the viral DNA/RNA sequence to control which of the synonymous codons is used for a particular amino acid. In other words, ribosome movement on mRNA is not uniform, and such "translational nonuniformity" is believed to affect protein folding.

Two features specific to multicellular organisms have recently been discovered: (i) the existence of intercellular and tissue specific variations in codon usage and tRNA abundance; and (ii) the existence of a dual program for translation regulation in cellular proliferation and differentiation coordinating tRNA supply and demand. It was found that tRNAs that are induced in proliferating cancer cells are typically repressed in differentiating/arresting cells. Conversely, the tRNAs that are induced in differentiating cells are often found to be repressed in proliferating cells, thus providing a necessary tuning of the tRNA supply to its demand adjusted to the characteristic codon-usage preference of the differentiation-related genes. Thus, the protein expression of many viruses in cancer cells will be altered or reduced, because the difference in tRNA abundance will change the translation kinetics, which can also affect the folding of the viral proteins.

Synthetic targeted viruses, or systemic targeted remedies (STRs), take the above two observations into account. Based on these observations, it is possible to change the level of viral protein(s) expression and viral protein folding by a given virus in a given cell type by the appropriate selection of synonymous codons with the goal of producing synthetic viruses that can be better expressed in cancer cells, but not in the non-malignant/normal cells. The synonymous codons of the viral ORFeome are adjusted so that the resulting translation kinetics are fine-tuned in cancer cells and more optimally matched to ensure enhanced expression and correct folding of the viral proteins in the cancer cells given differences in the repertoire of tRNAs in the cancer cells in comparison with the normal cells. This is done by suitable selection of both rare and frequent synonymous codons along the viral genome for each individual viral gene, taking into account the abundance of the tRNAs within the cancer cell type. As a result, the virus can reproduce within, and kill, cancer cells more efficiently. It is also expected that due to this optimization for the environment within a given cancer cell type, that the expression of the viral proteins and their folding will also be attenuated in normal cells, since the relative distribution of tRNAs is different and so the kinetics of translation will differ. In the normal cell, in addition to reduced expression of viral proteins, viral protein misfolding, and/or enhanced degradation can occur instead.

These synthetic targeted viruses, or STRs, can be produced by a reverse genetic approach that adjusts the codons in a "reference" virus in a way that leads to an attenuated expression of viral proteins in normal cells and their enhanced expression in cancer cells. The usage of synonymous codons thus ensures the correct folding for the viral proteins in cancer cells, which is important for gaining a mature and fully functional protein state. The approach also allows for a targeted optimization of certain/specific viral genes aimed at further modulation and attenuation of viral propagation and/or modulation of viral protein folding, therefore changing virus activity through targeted modulation of only a specific gene or a set of genes. As noted above, if necessary, targeted deoptimization/attenuation of only selected viral proteins (e.g. responsible for cellular lysis) can be specifically done with the aim of e.g. prolonging viral replication, specifically, in cancer cells. Furthermore, the codon optimization approach may consider cancer tissue-specific differences in tRNA usage/synonymous codon frequencies, so that the synthetic targeted viruses can be specifically targeted to a particular form of malignant disease.

Briefly, the following Table A identifies codon usage frequencies of the ORFeome of the natural Strain 1 Sabin FDA poliovirus and shows (i) the amino acid coded by each codon, (ii) the synonymous codons of the given amino acid and (iii) the relative frequency of the codon per one thousand codons. Codon usage was tabulated using count codon program http://www.kazusa.or.jp/codon/countcodon.html. This codon usage is believed to be optimal for viral replication in normal differentiated non-malignant cells/tissues. Note that Sabin strains are significantly attenuated in the central nervous system but are believed (and were shown) to replicate at wild-type levels in other cells/tissues like e.g. gut. These strains do not also grow well in cultured neuroblastoma cells.

TABLE A

Poliovirus Strain 1 Sabin FDA codon usage

| Amino Acid | Codon | Frequency/ 1000 | Amino Acid | Codon | Frequency/ 1000 |
|---|---|---|---|---|---|
| Gly | GGG | 14.48 | Trp | TGG | 12.67 |
| Gly | GGA | 21.72 | End | TGA | 0.00 |
| Gly | GGT | 17.19 | Cys | TGT | 10.41 |
| Gly | GGC | 11.31 | Cys | TGC | 8.60 |
| Glu | GAG | 22.17 | End | TAG | 0.45 |
| Glu | GAA | 28.96 | End | TAA | 0.00 |
| Asp | GAT | 24.43 | Tyr | TAT | 18.10 |
| Asp | GAC | 28.05 | Tyr | TAC | 25.79 |
| Val | GTG | 26.24 | Leu | TTG | 16.29 |
| Val | GTA | 12.67 | Leu | TTA | 10.86 |
| Val | GTT | 10.41 | Phe | TTT | 18.10 |
| Val | GTC | 13.12 | Phe | TTC | 20.36 |
| Ala | GCG | 7.69 | Ser | TCG | 4.52 |
| Ala | GCA | 27.15 | Ser | TCA | 21.72 |
| Ala | GCT | 22.17 | Ser | TCT | 9.05 |
| Ala | GCC | 15.84 | Ser | TCC | 15.38 |
| Arg | AGG | 10.86 | Arg | CGG | 3.17 |
| Arg | AGA | 21.72 | Arg | CGA | 1.36 |
| Ser | AGT | 9.05 | Arg | CGT | 3.62 |
| Ser | AGC | 8.60 | Arg | CGC | 2.71 |
| Lys | AAG | 28.05 | Gln | CAG | 19.46 |
| Lys | AAA | 28.51 | Gln | CAA | 17.19 |
| Asn | AAT | 22.17 | His | CAT | 8.60 |

TABLE A-continued

Poliovirus Strain 1 Sabin FDA codon usage

| Amino Acid | Codon | Frequency/ 1000 | Amino Acid | Codon | Frequency/ 1000 |
|---|---|---|---|---|---|
| Asn | AAC | 31.22 | His | CAC | 14.93 |
| Met | ATG | 30.32 | Leu | CTG | 15.38 |
| Ile | ATA | 15.84 | Leu | CTA | 15.38 |
| Ile | ATT | 23.98 | Leu | CTT | 9.50 |
| Ile | ATC | 20.81 | Leu | CTC | 12.22 |
| Thr | ACG | 6.79 | Pro | CCG | 5.88 |
| Thr | ACA | 21.72 | Pro | CCA | 24.89 |
| Thr | ACT | 23.08 | Pro | CCT | 13.57 |
| Thr | ACC | 24.43 | Pro | CCC | 9.05 |

Next, Table B below shows the codon usage in rapidly proliferating cancer cells (colon/bladder cancer cells) inferred from the tRNA pool of these cells. High-throughput methods are available in the art to produce such tRNA distribution profiles. This is provided only for purposes of illustrating the present disclosure.

Rapidly proliferating cancer cells codon usage frequency

| Amino Acid | Codon | Frequency/ 1000 | Amino Acid | Codon | Frequency/ 1000 |
|---|---|---|---|---|---|
| Gly | GGG | 19.00 | Trp | TGG | 12.67 |
| Gly | GGA | 35.00 | End | TGA | 0.00 |
| Gly | GGT | 20.00 | Cys | TGT | 60.00 |
| Gly | GGC | 25.00 | Cys | TGC | 40.00 |
| Glu | GAG | 45.00 | End | TAG | 0.45 |
| Glu | GAA | 55.00 | End | TAA | 0.00 |
| Asp | GAT | 58.00 | Tyr | TAT | 59.00 |
| Asp | GAC | 42.00 | Tyr | TAC | 41.00 |
| Val | GTG | 40.00 | Leu | TTG | 17.00 |
| Val | GTA | 18.00 | Leu | TTA | 13.00 |
| Val | GTT | 27.00 | Phe | TTT | 57.00 |
| Val | GTC | 16.00 | Phe | TTC | 43.00 |
| Ala | GCG | 6.00 | Ser | TCG | 4.00 |
| Ala | GCA | 32.00 | Ser | TCA | 19.00 |
| Ala | GCT | 32.00 | Ser | TCT | 22.00 |
| Ala | GCC | 30.00 | Ser | TCC | 16.00 |
| Arg | AGG | 20.00 | Arg | CGG | 15.00 |
| Arg | AGA | 31.00 | Arg | CGA | 14.00 |
| Ser | AGT | 20.00 | Arg | CGT | 9.00 |
| Ser | AGC | 19.00 | Arg | CGC | 11.00 |

-continued

| Rapidly proliferating cancer cells codon usage frequency | | | | | |
|---|---|---|---|---|---|
| Amino Acid | Codon | Frequency/ 1000 | Amino Acid | Codon | Frequency/ 1000 |
| Lys | AAG | 50.00 | Gln | CAG | 64.00 |
| Lys | AAA | 50.00 | Gln | CAA | 36.00 |
| Asn | AAT | 58.00 | His | CAT | 55.00 |
| Asn | AAC | 42.00 | His | CAC | 45.00 |
| Met | ATG | 30.32 | Leu | CTG | 28.00 |
| Ile | ATA | 23.00 | Leu | CTA | 10.00 |
| Ile | ATT | 43.00 | Leu | CTT | 17.00 |
| Ile | ATC | 34.00 | Leu | CTC | 14.00 |
| Thr | ACG | 8.00 | Pro | CCG | 6.00 |
| Thr | ACA | 32.00 | Pro | CCA | 35.00 |
| Thr | ACT | 33.00 | Pro | CCT | 34.00 |
| Thr | ACC | 27.00 | Pro | CCC | 24.00 |

Next, the relative codon usage/tRNA distribution frequencies between the reference virus ORFeome of Table A ("naturally" optimized for expression in "normal/given" human cells) and the ORFeome of cancer cells shown in Table B can be used to optimize/deoptimize a given nucleotide sequence from one cell type to another cell type. Optimization can be done by introducing synonymous codons that have the most similar usage frequencies in the native and target cells. Both rare and frequent codons are altered so as to obtain mRNA translation kinetics in the target cell that mimic the one observed in the native cell. Deoptimization is done by introducing synonymous codons that have the most dissimilar usage frequencies in the native and target cells, so that their translation kinetics differ as much as possible.

Strictly as an example, Table C provides a "native" original codon usage frequencies, target/cancer cell codon usage frequencies and the resulting optimized frequencies for the 10-codon sequence of the Strain 1 Sabin FDA poliovirus.

TABLE C

| Codon # | Original Codon | Original Codon Usage Frequency | Target Cell Codon Usage Frequency for Original Codon | Resulting/ Optimized Frequency | Optimized Codon |
|---|---|---|---|---|---|
| 1 | ATG | 30.32 | 30.32 | 30.32 | ATG |
| 2 | GGT | 17.19 | 20.00 | 19.00 | GGG |
| 3 | GCT | 22.17 | 32.00 | 30.00 | GCC |
| 4 | CAG | 19.46 | 64.00 | 36.00 | CAA |
| 5 | GTT | 10.41 | 27.00 | 16.00 | GTC |
| 6 | TCA | 21.72 | 19.00 | 22.00 | TCT |
| 7 | TCA | 21.72 | 19.00 | 22.00 | TCT |
| 8 | CAG | 19.46 | 64.00 | 36.00 | CAA |
| 9 | AAA | 28.51 | 50.00 | 50.00 | AAG |
| 10 | GTG | 26.24 | 40.00 | 27.00 | GTT |

Figure 3:
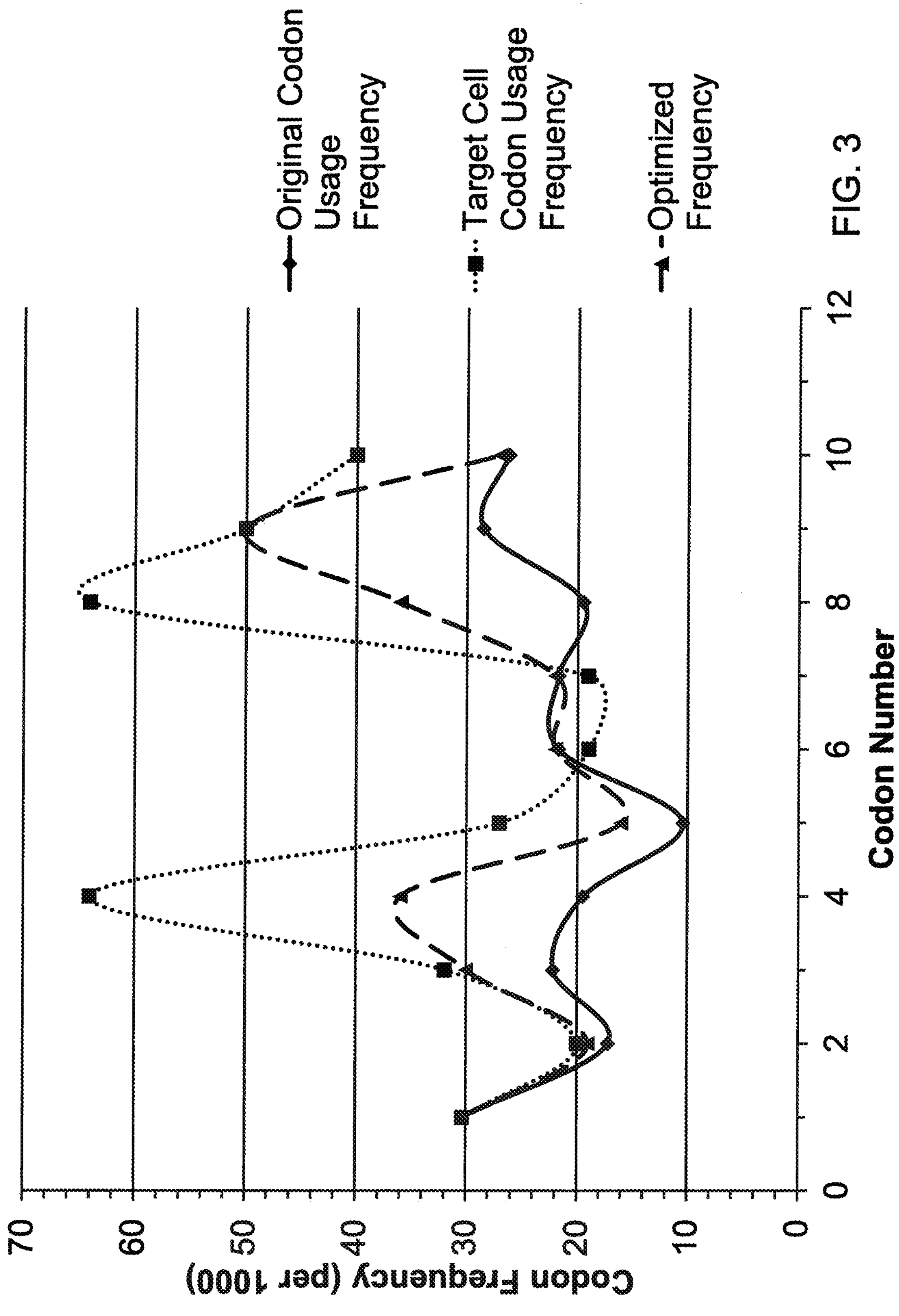
FIG. 3 is an example of a codon-usage profile, i.e. a graph of codon frequency (y-axis) vs. codon position (x-axis), for (a) a native poliovirus sequence (Strain 1 Sabin) (diamonds); (b) the native Strain 1 Sabin sequence in human cancer cells (codon usage inferred from tRNA populations observed in cancer cells) (squares) and (c) an optimized sequence that encodes for the same polyprotein as the native sequence, but optimized for the tRNA repertoire observed in cancer cells (triangles).

Referring now to Table C, the 10-codon sequence codes for a beginning of a poliovirus polyprotein that is desired to be expressed in cancer cells. In the column titled "Original Codon Usage Frequency", the frequency of the "original" codon in the natural virus believed to be "naturally optimized" for expression in a differentiated human cell/tissue is listed. In the column titled "Target Cell Codon Usage Frequency for Original Codon", the frequency of the "original" codon in target/rapidly proliferating cancer cells is listed. As can be seen by comparing these two columns, some of the codons vary greatly in their frequency. For example, the frequencies of codons #8 and #10 vary dramatically (64.00 vs. 19.46, and 40.00 vs. 26.24, respectively). Referring to FIG. 3, the difference in these codon frequencies is also evident.

The fifth column is titled "Resulting/Optimized Frequency", and shows the frequency of the codons in a 10-codon sequence that is optimized to express the same viral protein, but in the target/cancer cells.. The "optimized" codon for each position in the optimized sequence is determined as follows. First, for each pair of codons, the difference between their frequencies (target codon minus original codon) is determined and the synonymous codon in the target codon usage table is chosen with a frequency closest to the native sequence. Second, if the frequencies of several synonymous codons in the target cell are identical so that a selection based on frequency (solely) could not be made, a synonymous codon with a triplet composition minimizing wobbling at the third base should be chosen. Third, if the target synonymous codon already has the frequency closest to the native host frequency, it remains unchanged (note that sometimes this frequency can still be quite different from the native/original host).

For example, following the rules above, the GTG codon encoding Val at position 10 in the native sequence has been replaced with GTT in the optimized codon sequence. Val is encoded by four synonymous codons, and the GTT codon usage frequency (27.00) is the closest match (in the target cancer cell) to the original codon usage frequency (26.24) observed in the viral ORFeome.

In the case of codon #9 AAA (encoding Lys), the frequencies of the two Lys synonymous codons appear to be identical (50.00) in the target cancer cell. Thus, in this case, selection of an AAG codon was made to minimize wobbling at the third base of the codon triplet (as described above). Thus, AAA was replaced by AAG. The specificity of the decoding process is such that perfect Watson-Crick base pairs are usually observed between the first two nucleotides in the codon and those in the anticodon, but altered base pairing is possible at the third, so-called "wobble", position. Wobbling occurs because the conformation of the tRNA anticodon loop permits flexibility at the first base of the anticodon. Perfect Watson-Crick base pairing at the third codon base ensures high stringency of the decoding process and minimizes miscoding errors. Note also, that while the frequency of AAA and AAG codons in cancer cells is not a match for that of the native viral ORFeome no other selection is possible, since Lys is only encoded by these two synonymous codons.

Figure 4:
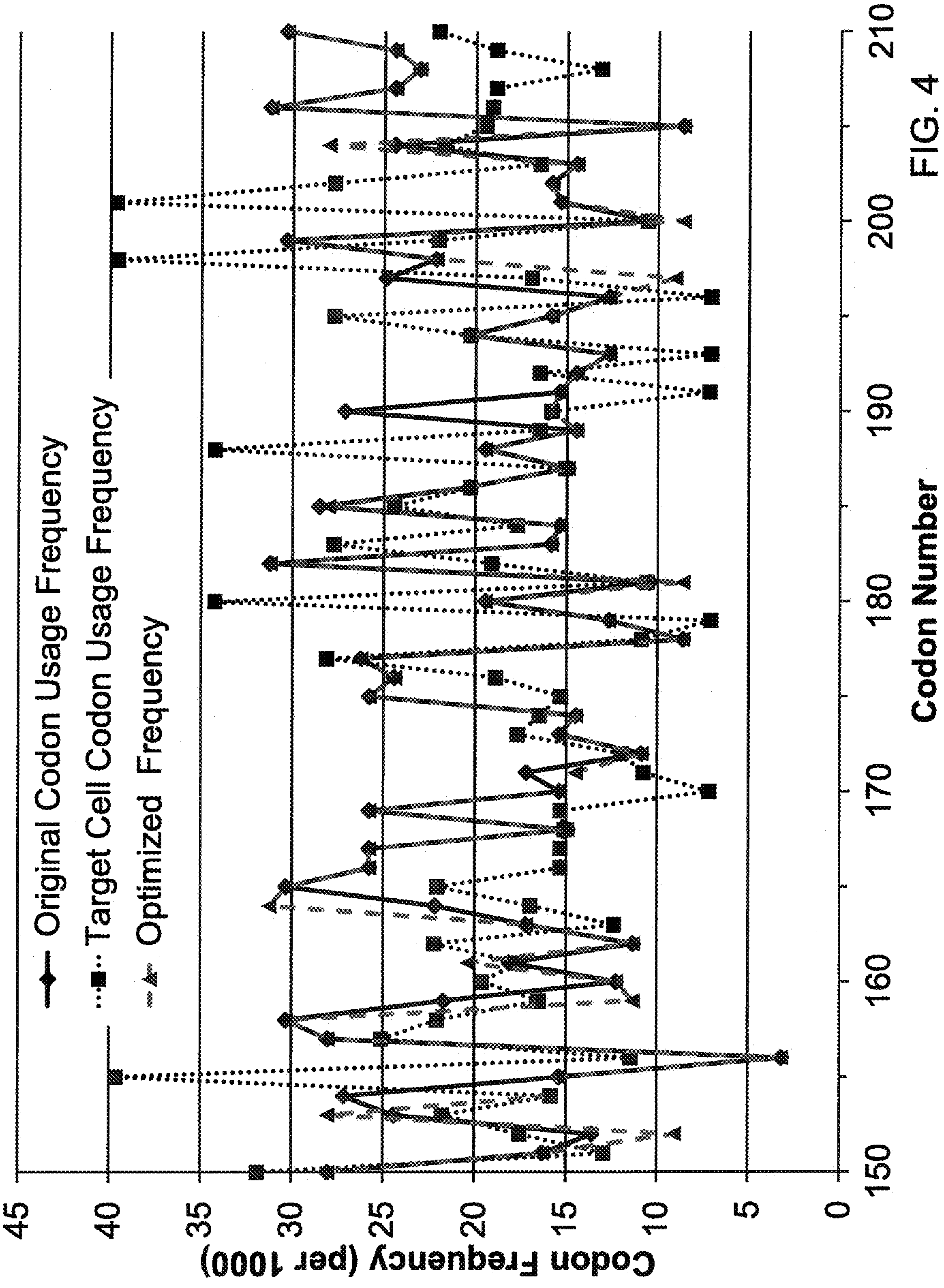
FIG. 4 is a larger codon-usage profile for (a) the native Strain 1 Sabin sequence in human cells (diamonds); (b) the native Strain 1 Sabin sequence in cancer cells (squares); and (c) the optimized sequence (triangles). In this graph, codons 150-210 are shown.

As a result of this optimization, as seen in Table C, nine of the 10 codons in the "native/reference" sequence encoding for this viral polyprotein are changed in the sequence optimized to encode for the viral protein to be expressed in cancer cells (note this comparison is presented strictly as an example). Looking at FIG. 3, the shape of the line for the "Optimized" (triangles) is desirably as close to that of "Original" (diamonds) as possible. FIG. 4 is a larger profile showing the results of this same optimization carried out on a larger scale. Here, codons 150-210 of the native and optimized sequences are shown. Again, desirably the line for the "Optimized" (triangles) is as close to that of "Original" (diamonds) as possible.

In the same manner, an entire ORFeome of the synthetic targeted virus can be derived from a "reference" virus. It is noted that only protein-encoding (open reading frame) regions of the virus need to be optimized. Other regions, e.g. 5' and '3 untranslated (UTR) regions, such as the 5'-Internal Ribosome Entry Site (IRES) elements, generally do not need to be optimized following this process. Note, however, that certain protein coding regions inside the ORFeome may not need to be optimized either. These regions may include critical RNA structural and/or sequence elements important for viral replication and function. These regions should be preserved intact, unless compensatory synonymous mutations restoring the structure or critical composition of these regions could be introduced.

In particular embodiments, the reverse engineered STRs are less than 85% identical (on the nucleotide level) to their natural analogs. In particular embodiments, the STRs may have less than 80% nucleotide identity, or less than 75% nucleotide identity to their natural analog. Generally, however, the STR or synthetic targeted virus has at least 67% nucleotide identity with the reference virus.

In such cases of low level identity to the natural analogs, the synthetic STRs could be considered a new genera of viruses and are presumed to be safe and not to be able to recombine with the natural viruses.

The present disclosure is further illustrated in the following non-limiting working examples, it being understood that these examples are intended to be illustrative only and that the disclosure is not intended to be limited to the materials, conditions, process parameters and the like recited herein.

EXAMPLES

A panel of twelve (12) non-pathogenic human viruses with oncolytic properties, Systemic Autonomous Targeted Oncolytic Remedies (SATORs) or Systemic Targeted Remedies (STRs), their isolation, and use is described below. Also presented is the composition and use of synthetic oncolytic viruses as a medicament in the treatment of cancer, wherein the synthetic oncolytic viruses were produced de novo with a modified nucleotide composition/synonymous codon usage.

Isolation of Virus Strains

A panel of non-pathogenic oncolytic viruses was formed by isolation from feces of healthy two to three year old children. The virus strains were isolated as follows: i) samples of feces were collected and stored for up to 48 hours at 4° C.; ii) feces were homogenized in HBSS (Hanks Balanced Salt Solution) to produce a 30% suspension; and iii) the suspension was cleared by centrifugation at 5000 g for 30 minutes and passed through a 0.22 ρ filter and stored at −70° C.

Monolayers of three cell cultures were prepared for virus isolation. These were: African green monkey kidney cell line CV1 (ATCC CCL-70); human carcinoma cell line HEp-2 (ATCC CCL-23); and human rhabdomyosarcoma cell line RD (ATCC CCL-136).

100 ml flasks with fresh monolayers of the cell lines were incubated with 1 ml of inoculum for 1 hour at 37° C., then washed three times with HBSS and incubated in DMEM with 1% FBS for 3 days. The flasks were then placed at −70° C. then thawed, and virus-containing medium was used for inoculation of fresh cell cultures, as above. Blind passages were repeated until cytopathic effect was visible at least in one type of cell culture. The viruses were collected and stored at −70° C. For routine propagation of the viruses CV1 (monkey kidney) cell line was chosen because it supported replication of all isolated virus strains. Virus titers were also determined in CV1 cells. They were in the range of 6-9 log TCD 50/ml.

Serotyping of the strains was performed by neutralization with type-specific sera. The following strains were obtained: STR4E1 (corresponding to Echovirus 1); STR6E7 (corresponding to Echovirus 7); STR7E12 (corresponding to Echovirus 12); STR8CA7 (corresponding to Coxsackievirus A7); STR9CA9 (corresponding to Coxsackievirus A9); STR10CB1 (corresponding to Coxsackievirus B1); STR11CB2 (corresponding to Coxsackievirus B2); STR12CB3 (corresponding to Coxsackievirus B3); STR13CB4 (corresponding to Coxsackievirus B4); STR14CB5 (corresponding to Coxsackievirus B5); and STR15CB6 (corresponding to Coxsackievirus B6); STR17E21 (corresponding to Echovirus 21).

The isolated virus strains belong to the Picornaviridae family, virus genus. These are small positive-sense, single-stranded RNA viruses 20-25 nm particles composed of four capsid proteins and a small VPG protein covalently attached to the genomic RNA of 7200-7300 nucleotides.

After isolation, the viruses underwent multiple passages in cell culture resulting in adaptation, higher yields of viruses and increase in titers of produced virus stocks.

Safety of the strains was tested on healthy volunteers per oral or intranasal application of $10^8$ PFU of the viruses. The tests have shown no severe adverse reactions and only rare incidences of minor flu-like symptoms that included moderate fever lasting for less than 24 hours (37.0° C.-37.5° C.), chills, nausea, and even less rare cases of mild diarrhea.

Safety of the viruses was also confirmed by published reports summarizing results of clinical trials, as they were used for mass non-specific protection against seasonal viral infections.

Propagation of Isolated Virus Strains in Tumor-Derived Cells

After purification from individual plaques, the abilities of virus strains to replicate in different tumor-derived human cell lines was tested using a panel of cell lines.

The tests were performed in 12-well plates with fresh sub-confluent monolayers of the cell lines. The cells were infected with 0.1 TCID50 per cell in 100 μl volume for 1 hour, then washed with HBSS and incubated in 1 ml of DMEM supplemented with 1% FBS. After 48 hours, monolayers displaying varying degrees of cytopathic effect were freeze-thawed and titers were determined by end-dilution and infection of CV1 cells.

Tables 1 and 2 below shows the propagation potentials of viruses from the panels shown as virus titers obtained on different cell lines: normal human embryonic lung fibroblasts (NHELF); breast carcinoma (BC); cervical carcinoma (CC); epidermoid carcinoma (EC); prostate carcinoma (PC); melanoma (Mel); non-small cell lung carcinoma (NSCLC); pancreatic carcinoma (PanC); and rhabdomyosarcoma (RMS).

TABLE 1

| | Virus titers produced by different cell lines (PFU/ml) | | | | |
|---|---|---|---|---|---|
| Virus Strain | IMR90 (NHELF) | HeLa (CC) | C-33A (CC) | MB231 (BC) | MCF7 (BC) |
| STR4E1 | 2 x $10^5$ | $10^8$ | $10^9$ | 2 x $10^8$ | 2 x $10^7$ |
| STR6E7 | $10^7$ | 5 x $10^7$ | 8 x $10^7$ | 2 x $10^7$ | 8 x $10^6$ |
| STR7E12 | $10^4$ | 2 x $10^7$ | 2 x $10^8$ | 5 x $10^8$ | 2 x $10^6$ |
| STR8CA7 | 2 x $10^8$ | 5 x $10^8$ | 2 x $10^9$ | 2 x $10^7$ | 5 x $10^6$ |
| STR9CA9 | <$10^2$ | $10^8$ | 2 x $10^7$ | 6 x $10^7$ | 2 x $10^4$ |
| STR10CB1 | 7 x $10^4$ | 6 x $10^4$ | 2 x $10^8$ | 2 x $10^8$ | 2 x $10^5$ |
| STR11CB2 | 2 x $10^4$ | 9 x $10^5$ | 6 x $10^7$ | 3 x $10^7$ | 6 x $10^6$ |
| STR12CB3 | 2 x $10^4$ | 3 x $10^4$ | 2 x $10^4$ | 2 x $10^4$ | 2 x $10^4$ |
| STR13CB4 | <$10^2$ | 2 x $10^7$ | 2 x $10^9$ | 6 x $10^7$ | 8 x $10^2$ |
| STR14CB5 | $10^5$ | 2 x $10^4$ | $10^7$ | 4 x $10^7$ | $10^4$ |
| STR15CB6 | <$10^2$ | <$10^2$ | 5 x $10^9$ | 5 x $10^6$ | <$10^2$ |
| STR17E21 | <$10^2$ | 2 x $10^3$ | 4 x $10^5$ | 4 x $10^5$ | $10^6$ |

TABLE 2

| | Virus titers produced by different cell lines (PFU/ml) | | | | | |
|---|---|---|---|---|---|---|
| Virus Strain | A431 (EC) | SK-Mel-28 (Mel) | A549 (NSCLC) | DU-145 (PC) | AsPC-1 (PanC) | RD (RMS) |
| STR4E1 | 5 x $10^5$ | 5 x $10^8$ | $10^7$ | 4 x $10^8$ | 2 x $10^7$ | $10^9$ |
| STR6E7 | 4 x $10^4$ | 5 x $10^8$ | 2 x $10^5$ | 2 x $10^7$ | $10^7$ | 5 x $10^8$ |
| STR7E12 | $10^7$ | 2 x $10^6$ | $10^6$ | 5 x $10^7$ | 2 x $10^8$ | 2 x $10^8$ |
| STR8CA7 | $10^4$ | 2 x $10^7$ | 2 x $10^6$ | 5 x $10^6$ | 2 x $10^3$ | 2 x $10^9$ |
| STR9CA9 | 2 x $10^4$ | $10^8$ | 8 x $10^7$ | 2 x $10^3$ | 4 x $10^4$ | 6 x $10^7$ |
| STR10CB1 | $10^7$ | 2 x $10^7$ | $10^6$ | 3 x $10^7$ | 4 x $10^6$ | $10^7$ |
| STR11CB2 | $10^5$ | $10^6$ | 2 x $10^5$ | 5 x $10^6$ | 2 x $10^6$ | 3 x $10^8$ |
| STR12CB3 | 2 x $10^4$ | 9 x $10^4$ | 2 x $10^4$ | 2 x $10^4$ | 3 x $10^4$ | 4 x $10^8$ |
| STR13CB4 | 4 x $10^3$ | 2 x $10^8$ | 6 x $10^5$ | $10^7$ | 2 x $10^8$ | 4 x $10^5$ |
| STR14CB5 | 2 x $10^5$ | 5 x $10^5$ | $10^6$ | $10^7$ | $10^6$ | 2 x $10^7$ |
| STR15CB6 | 4 x $10^3$ | $10^8$ | 2 x $10^5$ | 5 x $10^7$ | 5 x $10^7$ | <$10^2$ |
| STR17E21 | 3 x $10^6$ | 7 x $10^5$ | 2 x $10^6$ | 2 x $10^7$ | 6 x $10^6$ | 2 x $10^8$ |

The results presented in the above Tables 1 and 2 show that individual virus strains from the panel display overlapping but not identical propagation characteristics in different tumor-derived cell lines. In particular, MCF7 breast carcinoma cells do not support propagation of Coxsackieviruses B4 and B6/STR15CB6 but efficiently propagate Echoviruses 1 and 7. Coxsackieviruses A9 and B3 replicate poorly in AsPC-1 pancreatic cancer cells, although the cells are highly sensitive to Echovirus 12 and Coxsackievirus B4.

Example 1

Oncolytic Activity of Virus Strains in Nude Mice Xenograft Models

Methods and Materials

Figure 1B:
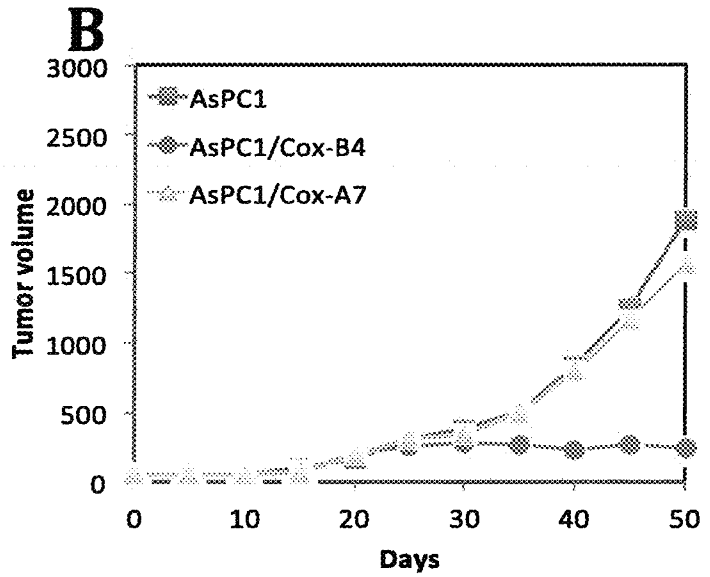
Figure 1C:
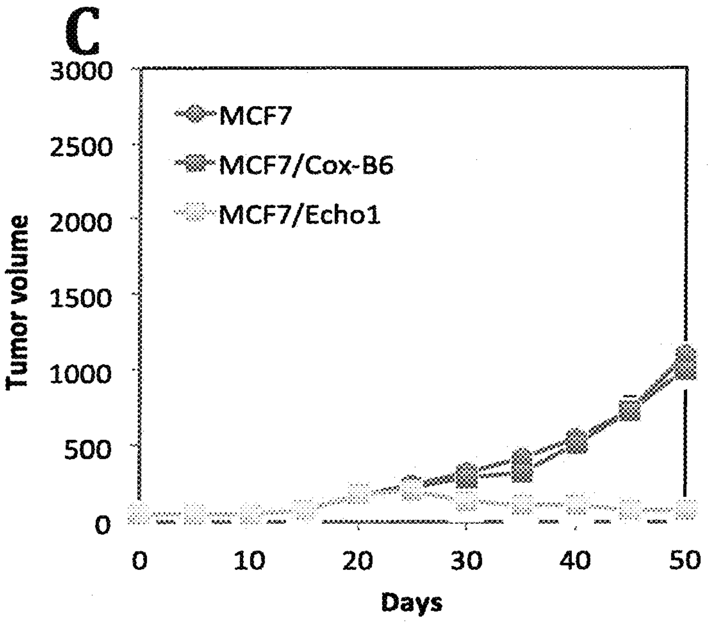
Figure 6:
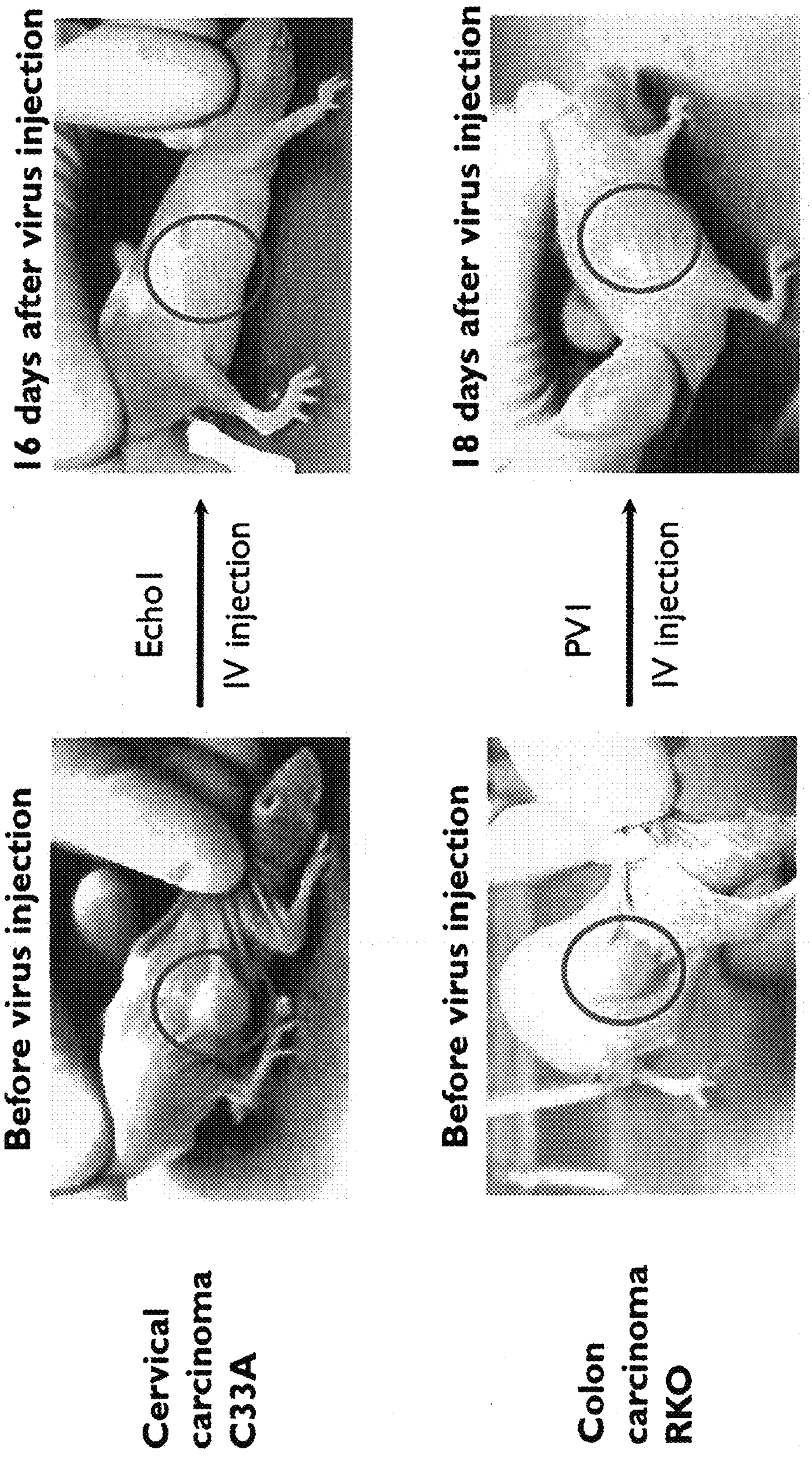
FIG. 6 is a set of four pictures showing viral potency against tumor cell growth in vivo in preclinical experiments involving immunocompromised (nude) mouse xenograft model. In the top row, cervical carcinoma (C33A) cells were injected subcutaneously, and Echovirus 1 was intravenously injected. The left photo is before virus injection, and the right photo is 16 days after virus injection. In the bottom row, colon carcinoma (RKO) cells were injected subcutaneously, and Poliovirus Strain 1 was then intravenously injected. The left photo is before virus injection, and the right photo is 18 days after virus injection.

The strains were further tested for oncolytic activity in athymic nude mouse xenograft tumors formed after injection with human carcinoma cells. Mice were injected subcutaneously with 2-10×$10^6$ cells. When tumor volume reached approximately 0.1-0.15 ml, tumors were injected with 0.05 ml of viruses ($10^8$ TCID50) daily for four days, and tumor volume was measured every 5 days until day 50. Control mice were injected with culture medium collected from uninfected cells. FIGS. 1A-1C are graphs with lines showing the growth of tumors over time (and are further discussed below) when untreated (C33A, AsPC1, and MCF7). FIG. 6 includes two pictures on the left showing tumor growth.

Results

A good correlation between the abilities of the viruses to propagate in the cell lines in vitro and the oncolytic activity in vivo was observed. The viruses that replicate poorly (Coxsackievirus B3 in C33A cells, Coxsackievirus A7/STR8CA7 in AsPC1 cells, Coxsackievirus B6/STR15CB6 in MCF7 cells) do not show oncolytic activity in xenograft tumors derived from the same cells, while the viruses that display strong replication (Coxsackievirus A7/STR8CA7 in C33A, Coxsackievirus B4 in AsPC1 and Echovirus 1 in MCF7 cells) are capable of destroying xenograft tumors.

FIG. 6 is a set of four pictures showing viral potency against tumor cell growth in vivo in preclinical experiments involving immunocompromised (nude) mouse xenograft model. In the top row, cervical carcinoma (C33A) cells were injected subcutaneously, and Echovirus 1 was intravenously injected. The left photo is before virus injection, and the right photo is 16 days after virus injection. In the bottom row, colon carcinoma (RKO) cells were injected subcutaneously, and Poliovirus Strain 1 was then intravenously injected. The left photo is before virus injection, and the right photo is 18 days after virus injection. As seen in the photos to the right, virus injection resulted in the tumors shrinking significantly.

Example 2

Testing Individual Sensitivity of a Patient's Malignant Cells to Different Strains of Oncolytic Viruses The examples demonstrate that oncolytic activities of individual strains of human viruses greatly varies depending on the nature of the cancer cells. Therefore, to achieve a positive response, an oncolytically potent virus strain needs to be chosen. This can be done directly by testing the sensitivity profile of short-term cultures of live malignant cells obtained by biopsy or surgery.

Materials and Methods

Samples of tumor tissue were collected into pre-chilled sterile medium DMEM supplemented with penicillin and streptomycin. The thickness of tumor fragments was less than 5 mm to provide good access for nutrients from the medium. The sample could be stored at +4° C. for up to 48 hours. It was then broken up into smaller fragments of 1-2 mm with a sterile rather blade and pushed through a nylon mesh of 50-100 micron size using a flat glass pestle. The suspension was then washed twice in the medium by centrifugation at 800 g for 5 minutes. The suspension was stained with Trypan blue and cells were counted. Equal portions of $1\text{-}5\times10^4$ cells in 0.2 ml were placed in sterile 1.5 mL plastic tubes and incubated with $1\text{-}5\times10^4$ TCID50 of different virus strains for 30 min at 37° C. The suspension was then washed three times with 1 ml of DMEM supplemented with 2% fetal bovine serum (FBS) at 800 g for 3 minutes in a microcentrifuge. Each sample in 0.2 ml was placed in two parallel wells of a 96-well plate and incubated at 37° C. in an atmosphere of 5% $CO_2$ and reduced oxygen for 48 hours. The samples were then frozen at −70° C., thawed, cleared from debris by centrifugation at 5000 g for 10 minutes at 4° C., and virus titer was determined by serial dilutions and infection of sensitive CV1 cells. Tumor samples displaying sensitivity to a particular human virus produced up to $10^6\text{-}10^7$ TCID50 per ml.

The technique for testing individual sensitivity to viruses is applicable to many different virus strains, including but not limited to human Echoviruses, Coxsackieviruses, Sabin strains of polioviruses, serotypes 1, 2 and 3, human reovirus type 1, human reovirus type, human reovirus type 3, Edmonston strain of measles virus, mumps virus, Newcastle disease virus strains, Sendai virus, Vaccinia virus strains, etc.

Example 3

Combination of Oncolytic Viruses for Simultaneous Applications

Figure 2:
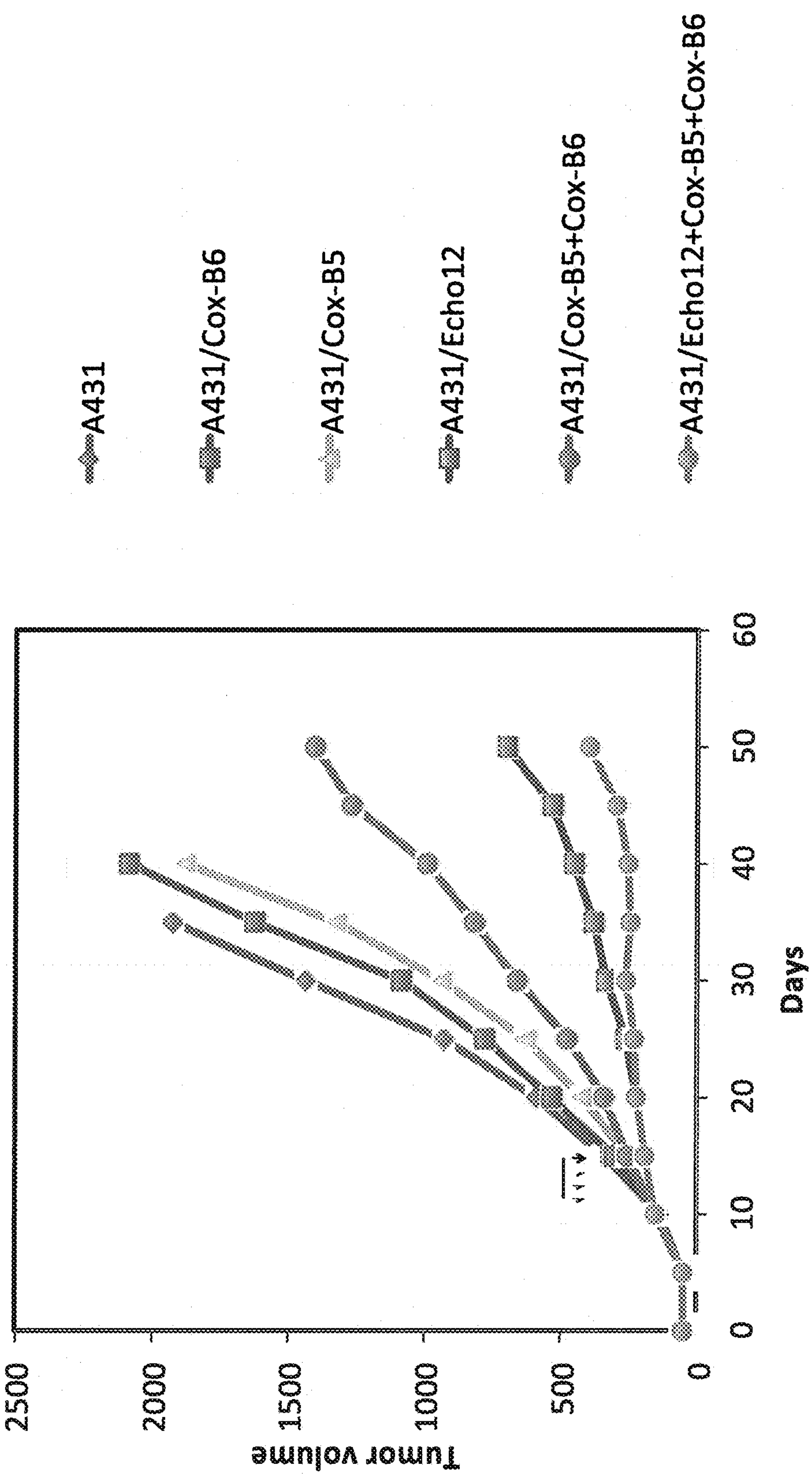
FIG. 2 is a graph indicating the effects of various combinations of viruses administered to mice injected subcutaneously with A431 epidermoid carcinoma cells. The y-axis runs from 0 to 2500 in intervals of 500. The x-axis runs from 0 to 60 in intervals of 10. The lines are for A431 alone (diamonds); Coxsackievirus B6 (Cox-B6, red squares); Coxsackievirus B5 (Cox-B5, green triangles); Echovirus 12 (Echo12, purple squares); Cox-B5+Cox-B6 (blue circles); and Echo12+Cox-B5+Cox-B6 (orange circles). For reference, the combination of all three viruses Echo12+Cox-B5+Cox-B6 (orange circles) always had a lower tumor volume than the two viruses Cox-B5+Cox-B6 (blue circles). The Cox-B6 values (red squares) always had a higher tumor volume than the Echo12 values (purple squares).

As shown in FIG. 2, the efficiency of simultaneous use of virus mixtures was demonstrated in xenograft experiments in nude mice bearing tumors derived from the C33A human cervical carcinoma cell line. Mice were injected subcutaneously with A431 epidermoid carcinoma cells. After tumors became palpable, the sites of tumors were injected with 0.1 ml of viruses ($10^8$ TCID50) with one-day intervals for four days. Cox-B5 corresponded to STR14CB5, Cox-B6 corresponded to STR15CB6, and Echo12 corresponded to STR7E12.

Mice were injected with single viruses (A431) displaying different propagation capacities in the cells and mixtures of two or three oncolytic viruses over one day intervals for four days. Tumor volume was then monitored until Day 50.

Example 4

Bioselection of Coxsackievirus 86 that can Replicate in MCF7 Cells

Materials and Methods

MCF7 breast carcinoma cells was found to be resistant to Coxsackievirus B6 producing less than $10^2$ PFU/ml 48 hours after infection with 0.1 PFU/cell of the virus (see Tables 1 and 2 above). Propagation of Coxsackievirus B6 virus was carried out in CV1 cells. For mutagenesis, a concentration of ribavirin that reduces the yield of infectious virus by 2 to 3 orders of magnitude in CV1 cells was determined. It corresponded to 0.1-0.5 mM. A fresh monolayer of CV1 cells was infected with 0.1 PFU/cell of Coxsackievirus B6 in the presence of ribavirin. Virus was collected after 24 hours, and MCF7 cells were infected with serial dilutions of the mutagenized virus. After 60 minutes absorption, the cells were washed with HBSS and then incubated for 48 hours in DMEM supplemented with 2% FBS. The virus collected from the sample represented the last dilution that displayed a cytopathic effect. It was then propagated in CV1 cells, and the obtained stock was used for the second round of mutagenesis and infection of MCF7 cells with serial dilutions.

Results

The virus stocks obtained from MCF7 and infected with the highest dilution of the virus displayed titers of $10^7\text{-}10^8$ PFU/ml when assayed in CV1 cells. Plaques in the plaque assay were polymorphous in appearance and in size. A larger plaque was taken and used for preparation of virus stock that demonstrated titers of $2\text{-}5\times10^8$ PFU/ml when propagated in MCF7 cells. The initial virus and the selected strain were sequenced. There were four amino-acid substitutions within the VP1 gene in the bioselected strain: Asn-655-->Lys; Thr-698-->Ile; Pro-715-->His and Lys-825-->Glu.

Example 5

Bioselection of Echovirus 1 that does not Cross-Neutralize with Antiserum

Materials and Methods

Antiserum for neutralization was obtained by immunization of sheep with concentrated purified stock of Echovirus 1. The antiserum was used for preparation of purified immunoglobulin. A mutagenized stock of Echovirus 1 was obtained in CV1 cells in the presence of 0.1 mM ribavirin. Dilutions of antibodies were incubated with the mutagenized Echovirus 1 stock at 37° C. for 60 minutes, and serial dilutions were used for infection of CV1 cells. Samples from the cells infected with the last dilution of antibodies and displaying cytopathic effect were used for second round mutagenizing with ribavirin and neutralization with antibodies and titration. Eight consecutive rounds of mutagenization and selection followed thereafter.

Results

During the next eight consecutive rounds of mutagenizing and selection there was a gradual increase in resistance of the viruses to neutralizing effects of antiserum. The selection was considered successful when the effect of antibodies against Echovirus 1 was similar to the effect of heterologous antibodies raised against poliovirus type 1.

Example 6

Generation of Synthetic STRs

Materials and Methods

Poliovirus live attenuated vaccine strain (Sabin strain type 1; FDA approved for oral poliovaccine) genome was codon optimized to attenuate viral expression in normal cells and enhance its proliferation in rapidly dividing/cancer cells. The modified genome was chemically synthesized, assembled and further used to produce live virus. SEQ ID NO: 1 is the nucleotide sequence for the reference wild-type Strain 1 Sabin. SEQ ID NO: 2 is the nucleotide sequence for the codon-optimized synthetic virus. There is 80.1% identity between the two nucleotide sequences (5316/6630 using CLUSTAL 0 v1.2.2).

Results

A set of synthetic modified polioviruses (STRps) with modified genomes was produced. Poliovirus has a single-stranded positive-sense RNA genome, which can act as mRNA (encoding a polyprotein), as a template for genomic RNA replication, or as a nascent genome to be packaged into virus particles. Expression of the viral genome and replication of the virus are critically dependent on the function of the so-called Internal Ribosome Entry Site (IRES)-element located in the 5-Untraslated Region (UTR) of the genomes. The IRES recruits the small ribosomal subunit to the vicinity of the initiation codon and initiates synthesis of a viral polyprotein. Upon cleavage, the N-terminal part of the polyprotein gives rise to the structural (capsid) protein, while the C-terminal part gives rise to a number of non-structural proteins, including an RNA-dependent RNA polymerase and a number of virus-specific proteases. Therefore, expression of viral capsid proteins along with titration of virus particles in the medium and measuring sizes of plaques in agar plaque assay can be used for comparing virus replication fitness in different cell types.

Figure 5:
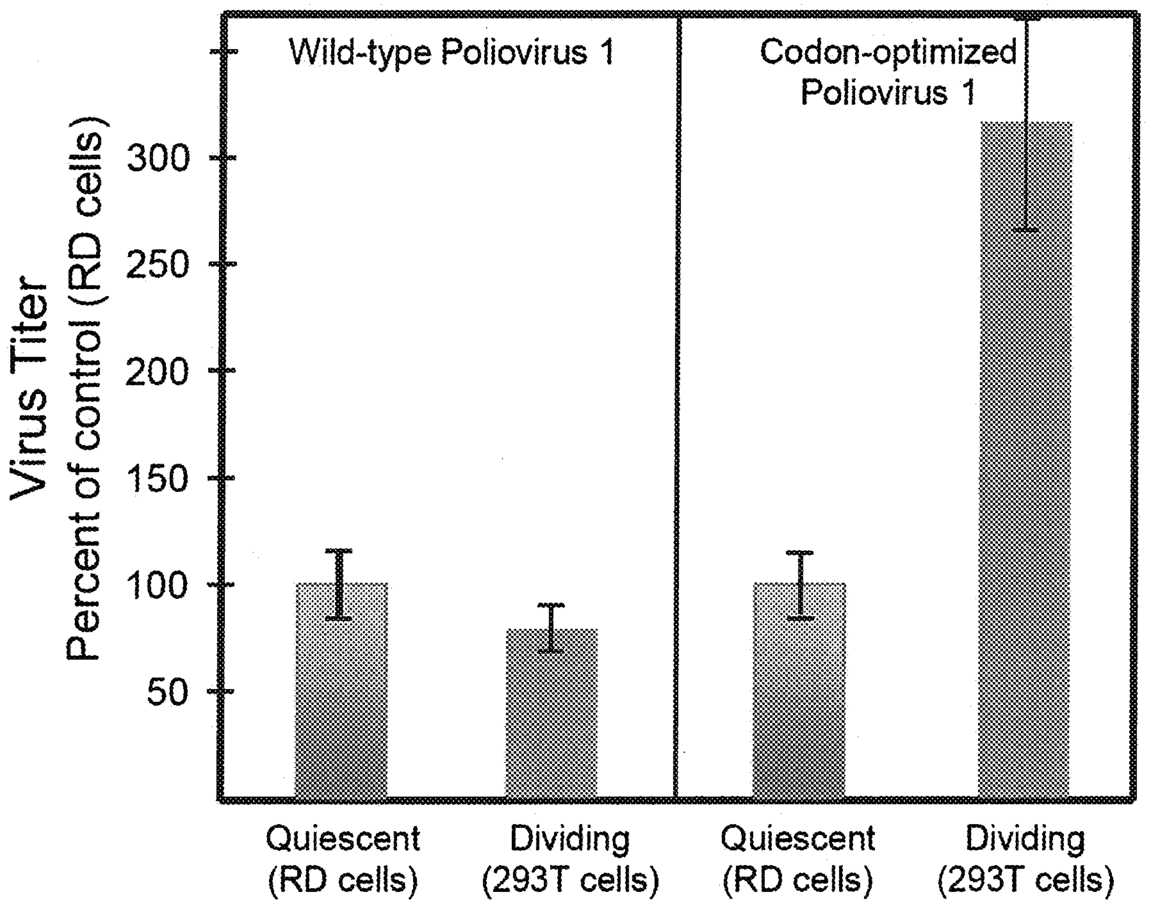
FIG. 5 is a histogram comparing unmodified Poliovirus 1 against codon-optimized Poliovirus strain 1 in Quiescent (RD cells) and exponentially-dividing 293T cells. The synthetic/codon optimized virus showed preferential (~3-fold higher) replication in dividing cells. The y-axis is the virus titer in percent of control cells, and runs from 0 to 350 in increments of 50.

The native Poliovirus strain 1 and the synthetic codon optimized Poliovirus strain 1 were compared for their ability to propagate in Quiescent (RD cells) and exponentially-dividing 293T cells. The RD cells acted as a control. As seen in FIG. 5, the synthetic/codon optimized virus showed preferential (~3-fold higher) replication in dividing cells.

Clinical Examples of Panels of Oncolytic Viruses in Single Patients

Example 7

Patient A. S., a 33 year old female, was diagnosed with T3N1M1 low-grade ovarian adenocarcinoma, peritoneal and pleural carcinomatosis, malignant ascites and pleuritis, multiple pelvic, abdominal and mediastinal metastases, and multiple lymphadenopathy.

The patient was treated with STRS1 (oncolytic strain of Sendai virus) for one year (12 weekly then 7 monthly intradermal injections of STRS1, $10^8$ I.U./ml). There was a drop in CA-125 marker over a period of 3 months from 2100 units to 30-50 units, and there were no signs of disease progression for 11 months, but then the CA-125 level started to rise and ascites fluid resumed the build up. The ascites fluid was taken for testing of the sensitivity of the cancer cells to a panel of available oncolytic viruses. The ex vivo testing was carried out as follows:

200 ml of ascites fluid supplemented with heparin to avoid fibrin clotting was centrifuged for 10 minutes at 2000 g, the sediment containing spheroid aggregates of cancer cells was collected and the cells were counted. There were approximately $7\times10^5$ cells in one ml of the fluid. The cells were washed with HBSS, divided in portions of $2\times10^6$ cells in 1 ml of DMEM and placed in 1.5 ml microtubes. The viruses were used for testing: Sabin strain of poliovirus type 1, Echoviruses STR4E1 and STR7E12, Coxsackieviruses STR8CA7 and STR14CB5, Reovirus Type 1 (STRR1), Measles virus, Edmonston-derived strain STRM1ESC. The cells were infected at a multiplicity of 0.1 TCID50 per cell, incubated for 60 minutes at 37° C., washed three times with HBSS, centrifuged at 800 g for 3 minutes, and placed in 1 ml of DMEM, 2% FBS at 37° C. in 5% $CO_2$. After 48 hours, complete degradation of cells was observed in all samples except mock-infected cells. Virus titers for most strains were determined using CV1 cells.

Titers of Sendai virus strain STRS1 were determined in the hemagglutination reaction, and by infecting MDCK cells in the presence of 10 μg/ml of trypsin. The cells from ascites fluid were considered as highly sensitive to all viruses used in the test producing virus titers in the range of $5\times10^7$-$5\times10^8$ TCID50 per ml. The cells also remained sensitive to STR-S1 producing $5\times10^5$ TCID50 per ml, which is considered as high sensitivity. However, the ascites fluid taken from the patient contained high titers of antibodies capable of neutralizing STR-S1 (more than 1:100,000), which was considered as the cause of the relapse.

The patient was then injected with $1\times10^8$ PFU of Echovirus 1 strain STR4E1 intravenously. Nine days after the injection, analysis of ascites fluid showed virtually no cancer cells. There was a gradual decline in CA-125 during the following 5 weeks, from 3500 to 350 units. However, starting week 6 after the injection, ascites fluid resumed the build-up, and cancer cells reappeared as spheroid aggregates. Ex vivo tests have determined that the cells retained full sensitivity to STR7E12, STR10CB3, STRR1 and STR-MESC1 but were resistant to STR4E1. There were neither visible cytopathic effects nor virus production following the infection with Echovirus 1 at 0.1 and 1 TCID50 per cell. It was concluded that the relapse was caused by a selection of cancer cells resistant to STR4E1.

The patient was then injected intraperitoneally with 10 ml of a cocktail of three viruses—$1\times10^8$ PFU each of STR10CB5, STR-R1 and STRMESC1 (Coxsackievirus B5, Reovirus Type 1, and Edmonston-derived Measles virus strains). Cytology tests of ascites fluid four days after the inoculation has shown no live cancer cells. No reappearance of cancer cells was detected two months after the inoculation.

Example 8

Patient M. C., a 74 year old male, was diagnosed with adenocarcinoma of Urachus, 2 years post resection, tumor spread near sigmoid colon, colonic obstruction (55 mm×35 mm; sigmoidal stent was introduced to overcome the obstruction) and to the ileocecal region (60 mm×30 mm), carcinomatosis of peritoneum, and ascites. By the time of the treatment the patient was in critical condition with rapid build-up of ascites, and the liquid build up in the scrotum.

50 ml of ascites fluid was centrifuged and inspected. It contained $2\times10^6$ cancerous cells per ml. The cells were washed and seeded in DMEM plus 10% FBS at a density of $2\times10^5$ cells per ml. In three days, the cells formed a monolayer and were further cultured by weekly splitting 1:3.

Reproduction of a set of viruses was tested in the cells. The cells (passage 1) were seeded into 24-well plates, infected with 1-5 PFU/cell of viruses the next day, and progeny viruses were collected 3 days later. Viruses were quantified by serial dilution titration in susceptible cells. The cells were highly susceptible to STRS1, STRR1, STR-MESC1, STR4E1, STR7E12, STR14CB5, STR15CB6, and resistant to STR8CA7.

Taking into account the critical condition of the patient, oncolytic virus preparation was introduced directly into ascitis fluid through intraperitoneal injection of 10 ml of Sendai virus strain STRS1, $2\times10^8$ I.E. per ml.

There was a rise of body temperature (18 hours post injection) to 38.7-39.4° C. Other symptoms included fatigue, nausea, slight and vague pains in the abdominal region. Temperature rise was efficiently blocked by paracetamol and maintained at 37.2° C. until becoming normal and subnormal during the next 24 hours. There was also an increase in urination during the next three days along with a decrease in ascites. Scrotal fluid disappeared during the first 48 hours, and ascites became non-detectable by day 4 after the injection. General condition and activity of the patient improved rapidly, with a good appetite, and a better mood.

35 days after the injection, PET-CT showed complete resolution of the tumor in the ileocecal region and substantial reduction of the tumor in sigmoidal colon region, with a residual local increase in metabolic activity in the region facing the sigmoidal stent.

60 days after the injection, the patient started to complain about partial obstruction between the stomach and duodenum leading to vomiting after meals. A liquid build-up was detected in the upper abdominal region because of the adhesive process initiated by the previous episode of ascites buildup. An abdominal puncture did not reveal any cancerous cells in the fluid. The condition was treated by diuretics and a more active regimen (e.g., daily walking).

The peritoneal adhesive process continued progressing during the next four months, leading to problems with bowel evacuation, slimming and weakness. To prevent possible recurrence of the malignant process the patient was injected intravenously with $2\times10^8$ PFU STRMESC1 (Edmonston-derived measles virus strain). There was a temperature rise 24 hours after the injection (37.2-37.4° C.) lasting for the next 18-20 hours then subnormal temperature (35.5° C.) lasting for three days and associated with fatigue. No other manifestations were observed. There was also no substantial improvement of the patient's condition. The major remaining problem was the adhesive process in the peritoneum. Eight months after the first oncolytic virus injection, the patient experienced a heart attack that added to the abdominal problems. The patient's condition continued to deteriorate, and the patient died 11 months after the start of oncolytic therapy. However, postmortem autopsy did not reveal live cancer cells in the region of the sigmoidal and ileocecal tumors, and there were signs of fibrosis in the regions of former tumors.

Example 9

Patient M. A., an 82 year old female, was diagnosed with sigmoidal adenocarcinoma, two years post resection, metastases to the liver, 25×15 mm and 20×10 mm, cachexia, and CEA—55 ng/ml.

No chemotherapy was applied to the patient. By the time of first injection the patient was weak, staying in bed. There were signs of jaundice.

The patient was injected intradermally with 1 ml of concentrated Sendai virus strain STRS1 ($10^9$ I.E./ml) mixed with cells obtained from a day 4 chicken embryo, $10^7$ cells. Twenty intradermal injections, 0.05 ml each, were made in the spinal region of the patient to increase exposure to the virus. Chicken embryo cells support replication of STRS1 virus, thereby prolonging the effect of the injection. The injections were repeated in 14 day intervals for three months.

There was no temperature rise or any other side effect in response to the injections. The patient's condition started to improve 5 to 7 days after first injection. There was an improvement of liver function (ALT/AST), disappearance of jaundice, improved energy, gain in weight (plus 7 kg to 55 kg total), the patient did not stay in bed, resumed active life, and spent three summer months in a country house performing a vegetable garden routine. Four months after the first injection, CT scans showed substantial shrinkage of liver metastases to barely detectable.

Nine months after the first injection, the patient's condition worsened with fatigue, anemia, and decreased erythrocyte count. No specific examination at tumor sites was made. The patient was injected intravenously with an oncolytic virus cocktail containing 108 PFU each of STR4E1, STR8CA7 and STR14CB5 (Echovirus 1, Coxsackievirus A7, Coxsackievirus B5 strains). There was a temperature reaction 18 hours after the injection (37.9° C.) lasting for 18 to 20 hours. The patient's condition started to improve 48 hours after the injection. Blood parameters (erythrocyte count and hemoglobin) reached normal levels two weeks after the injection. Six months after the injection, the patient was stable with no specific complaints. CEA=7 ng/ml.

Example 10

Patient N. S., a 36 year old female, was diagnosed with low grade squamous cervical carcinoma, metastases to Douglas space and ascites. The primary tumor was surgically removed two years previously. Metastases were detected four months before the oncolytic virus therapy.

The patient was injected intradermally with 1 ml of concentrated Sendai virus strain STRS1 ($10^9$ I.E./ml) in 20 spots in the spinal region. The injections were repeated every second week for five months. A temperature reaction was observed after the first injection (38.5° C.) lasting for one day. No temperature rise was observed during subsequent injections. There was a gradual improvement of the patient's condition. Ascites fluid disappeared during the first month. In three months, a CT scan showed a substantial shrinkage of tumor mass in the Douglas space. The patient's condition has remained stable for one year.

Example 11

Patient M. L., a 73 year old male, was diagnosed with prostate acinar adenocarcinoma, metastases to bones (vertebrae, ribs, pelvis). The primary tumor was not removed (21 mm×21 mm×13 mm). PSA=230 ng/ml.

Biweekly intradermal injections with concentrated Sendai virus strain STRS1 ($10^9$ I.E./ml) were administered across 20 locations mixed with $10^7$ day 4 chicken embryo cells over a period of 6 months. After four months, injections were administered twice a week four months. There was no temperature reaction. Patient's pains in bones gradually disappeared during the first 2 months. After 6 months a PET CT scan revealed no progression of the disease with somewhat diminished metabolic signals in metastases. Condition remained stable 1.5 years after the first oncolytic virus injection. PSA=41 ng/ml.

Example 12

Patient A. S., a 55 year old male, was diagnosed with prostate adenocarcinoma, which was surgically removed two year previously, and metastases to bones (pelvic, ribs, cranial). PSA=1400 ng/ml.

The patient was intramuscularly injected with 1 ml of concentrated purified preparation ($10^9$ PFU per ml) Echovirus 1 strain STR4E1.

There was a temperature reaction (39.5° C.) on days 3-4 and pain in tumor sites. The pain subsided by day 3. Injections were repeated with three week intervals. There was no temperature reaction after the repeated injections.

On Day 51, a CT scan revealed a reduction in tumor size, and evidence for bone obstruction repair. PSA dropped to 210 ng/ml.

On Day 65, the patient was administered with an intramuscular injection of concentrated purified Coxsackievirus B5 strains STR14CB5, 109 PFU per ml four times with three week intervals. There was a temperature reaction after the first injection, but the following injections were asymptomatic.

Six months after the treatment start, there was no progression of the disease, and the patient's condition was stable. PSA=105 ng/ml.

Example 13

Patient F. A., a 65 year old male, was diagnosed with prostate adenocarcinoma, which was surgically removed. A sample of the tumor was used for generation of a cell line. Prostate carcinoma cells were free of associated fibroblasts. The cell line was used for testing sensitivity to a panel of oncolytic viruses. The cell line was highly sensitive to STRS1, STRR1, STR4E1, STR8CA7, STR14CB5 but relatively resistant to STR7E12, STR15CB6 and STRMESC1.

Eight months after the surgical operation, the patient started complaining of pains in the pelvis region. A CT scan revealed bone metastases in the pelvis and ribs. PSA=1500 ng/ml.

The patient was injected intramuscularly with a concentrated and purified virus cocktail, $10^9$ PFU per ml each of STR4E1, STR8CA7 and STR14CB15 (Echovirus 1, Coxsackievirus A7, Coxsackievirus B5 strains). There was a temperature reaction after 18 hours (38.3° C.), the next day (37.5° C.), and day 3 (37.2° C.). Then a subnormal temperature reaction occurred for three days. The patient experienced pains in his pelvis and ribs lasting for one week then the pains subsided. The injection was repeated five times with three-week intervals.

PSA dynamics were as follows: 1500 ng/ml (start), 1700 ng/ml (10 days after the start), 670 ng/ml (35 days after the start), 205 ng/ml (3 months after the start), and 86 ng/ml (5.5 months after the start).

The patient's present condition (6 months after the start of treatment) is stable. The patient has no complains, and a CT scan provided evidence of bone repair in tumor sites.

Example 14

Patient A. A., a 72 year old male, was diagnosed with prostate carcinoma, four years after surgical removal, and metastases to lung and liver. Hormone therapy was initially efficient but was followed by a relapse with progressive growth of metastases. PSA=2500 ng/ml.

The patient was given biweekly intradermal injections with concentrated Sendai virus strain STRS1 (109 I.E./ml) in 20 locations mixed with $10^7$ day 4 chicken embryo cells over a period of 5 months. A temperature rise was observed during the first injection (39.2° C.) lasting for one day. A second injection resulted in a lower temperature (37.4° C.) lasting for 12 hours. There was no temperature reaction during the following rounds of injections. PSA dynamics were as follows: 2500 ng/ml (start); 2700 ng/ml (10 days after start); 930 ng/ml (33 days after start); and 220 ng/ml (4 months after start).

A second virus was applied 5 months after the start. Reovirus Type 1 strain STRR1 was injected intramuscularly ($2\times10^8$ PFU/ml, 2 ml) with two-week intervals for three months. There were no adverse reactions except a slight temperature rise (37.2° C.) and lasting for less than one day after the first injection. PSA: 270 ng/ml (Day 14); 184 ng/ml (Day 31); 56 ng/ml (Day 105).

Example 15

Patient E. B., a 44 year old female, was diagnosed with ovarian carcinoma six years ago with metastases to umbilical region, peritoneum, solid tumors in the peritoneal region (32 mm×16 mm; 52 mm×35 mm) and pleuritis. Metastases in the brain were removed by CyberKnife. The patient then underwent 12 rounds of chemotherapy. The patient then experienced relapse, during which two tumors in the abdomen (14 mm×9 mm and 23×16 mm) were discovered. CA-125-299.

The patient was injected with biweekly intradermal injections with concentrated Sendai virus strain STRS1 ($10^9$ I.E./ml) in 20 locations mixed with $10^7$ day 4 chicken embryo cells over a period of 2 months. Ultrasonic study revealed negative dynamics, although the patient's general condition had improved.

The patient was then injected with biweekly intramuscular injections of purified oncolytic virus cocktail: Echovirus type 12 strain STR7E12, Coxsackevirus type B3 strains STR12B3, and Reovirus Type 1 strain STRR1 ($10^8$ PFU each) for two months.

Ultrasonic examination revealed positive dynamics. At present the patient is receiving intramuscular injections of oncolytic virus cocktail containing Echovirus 1 strains STR4E1, Sabin Poliovirus Type 1 strain, and Newcastle virus derived strain STRNH1. The patient's condition has stabilized.

Example 16

Patient V. S., a 42 year old female, was diagnosed with breast carcinoma four years ago and underwent surgical resection. The patient was also diagnosed with metastases to liver, lungs, and peritoneum. The patient underwent 14 rounds of chemotherapy and relapsed. Three tumor sites in the liver (22 mm×14 mm; 26 mm×18 mm; 18 mm×20 mm) and in the lung (15 mm×18 mm) were found.

The patient was injected biweekly with intradermal injections with concentrated Sendai virus strain STRS1 ($10^9$ I.E./ml) in 20 locations mixed with $10^7$ day 4 chicken embryo cells over a period of 3 months. Ultrasonic study revealed positive dynamics, and tumors in the liver diminished to 12 mm×6 mm; 7 mm×6 mm and 5 mm×8 mm and in the lung to 4 mm×6 mm.

Example 17

Patient L. P., a 51 year old female, was diagnosed with gastric carcinoma four years ago and underwent surgical resection. Metastases to the upper lobe of right lung (32 mm×37 mm×28 mm) and multiple small metastases scattered throughout the left and right lungs have been revealed. Metastases to bones (Th9-L2, L4) were also revealed. CEA=367.2.

The patient was injected biweekly with intradermal injections of concentrated Sendai virus strain STRS1 ($10^9$ I.E./ml) in 20 locations mixed with $10^7$ day 4 chicken embryo cells over a period of 3 months. A CT scan showed a stabilization of the process and limited positive dynamics. Namely, the main metastases in the lung stabilized at 28 mm×25 mm×20 mm.

Starting at month 4, the patient was injected with biweekly intramuscular injections of an oncolytic virus cocktail, including 2 ml of a mixture containing purified Echovirus 1 strain STR4E1, Reovirus Type 1 strain STRR1 and Newcastle disease virus strain STRNH1 ($2\times10^8$ PFU each). The patient's condition stabilized.

Example 18

Patient K. I., a 52 year old female, was diagnosed with carcinoma of the fallopian tubes, metastases to lymph nodes and peritoneum, and ascites. The main tumor was surgically removed four years ago, and the patient's relapse started two years ago. Ten rounds of chemotherapy resulted in positive dynamics; however a second relapse has led to a rapid buildup of ascites fluid.

250 ml of ascites fluid was obtained by laparocentesis. The tumor cell count in the fluid was $2\times10^5$ cells per ml. The cells were washed with Hanks salt solution and seeded to plates at a density of $5\times10^5$ cells per ml in DMEM/F12 medium supplemented with 10% FBS. Most cells attached, and the plates reached confluence in three days. A portion of the cells was frozen in liquid N2, and the rest continued to grow in culture. A few individual clones were isolated and propagated frozen for experimental use in the future as well as for a source for specific tumor antigens of the patient. In addition, $2\times10^6$ of the ascites-recovered cells were mixed with Matrigel and injected subcutaneously into nude mice. Slowly growing tumors became visible four weeks after the inoculation.

The ascites-derived cancer cells were used for testing their sensitivities to a panel of oncolytic viruses. The cells were seeded to 24-well plates, reached sub-confluence, and infected with 1-5 I.E. per cell with different oncolytic viruses. Three days after the infection, the cells were scored for cytopathic effect then frozen-thawed and the released newly-propagated virus was quantified by serial dilution titration in sensitive cells (CV1 and MDCK, depending of the virus strain).

The cells were found highly sensitive to the following viruses: Sabin Poliovirus Type 1 strain, STR4E1, STR13CB4, STR15CB6, STRR1, STRNH1, and STRMESC1. The cells were found to be partially sensitive to STR7E12, STR8A7, STR14CB5, and STRR2. The cells were found to be resistant to STRS1, STR17E21, STRMuVD1 (oncolytic Mumps virus strain), and STRCDV1 (oncolytic canine distemper virus strain).

Based on the data, two oncolytic virus panels were formed. Panel 1 consisted of STR4E1, STR13CB4, and STRR1. Panel 2 consisted of STR15CB6, ATRNH1, and STRMESC1. Panel 1 (2 ml) was injected intramuscularly in biweekly intervals, $2\times10^9$. There was a notable improvement of the patient's condition after two months of the treatment. Ascites fluid stopped building up and was no longer detected by ultrasonic examination. General condition of the patient also improved.

Example 19

Patient D. N., a 54 year old male, was diagnosed with stage four pancreatic cancer, and no chemotherapy or surgery was administered. The tumor was located in the pancreatic body (38 mm×45 mm×24 mm) with sharp margins. A small amount of ascites fluid, hydrothorax at the left, obstruction of choledochus was relieved by a stent. CA 19-9=4557 U/ml, CEA=8.08 ng/ml.

The patient received biweekly intradermal injections with concentrated Sendai virus strain STRS1 ($10^9$ I.E./ml) in 20 locations mixed with 10' day 4 chicken embryo cells, over a period of 2 months. By the end of month 2, CA-19-9 increased and reached 9845 U/ml.

The oncolytic virus cocktail was then changed to one containing Echovirus 1 strain STR4E1, Reovirus Type 1 strain STRR1, and Coxsackevirus A7 strain STR8CA7, ($2\times10^8$ PFU each). The oncolytic viruses (2 ml) were injected biweekly intramuscularly. The CA-19-9 dynamics were as follows: 9845 U/ml (start); 9567 U/ml (day 32); and 5764 U/ml (day 75).

Example 20

Patient L. N., a 58 year old female, was diagnosed with ovarian carcinoma four years ago. A surgical resection of the ovary and uterus were done. The patient was also diagnosed with metastases to peritoneal lymph nodes and ascites.

Ascites fluid was collected and inspected. No live cancer cells were detected. As there was a rapid buildup of ascites fluid, STRS1 virus was injected intraperitoneally by laparocentesis (10 ml containing $10^9$ I.E. of the virus). The temperature reaction was as follows: 38.9° C. (day 2); 37.8° C. (day 3); and 37.2° C. (day 4), then subnormal for three days. Ascites buildup slowed down by day 4 and was barely detectable by day 25. General condition of the patient improved. Starting day 14, the patient was administered biweekly intradermal injections with concentrated Sendai virus strain STRS1 ($10^9$ I.E./ml) in 20 spots mixed with $10^7$ day 4 chicken embryo cells. The patient's condition stabilized.

Example 21

Patient K. S., a 68 year old female, was diagnosed with stage four pancreatic cancer (with the primary tour in the pancreatic head region), and metastases to para-pancreatic lymph nodes, spleen (resected 13 months ago), peritoneum, mediastinal lymph nodes, and left adrenal gland. CA-19-9 marker at the beginning of the treatment was 243. Chemotherapy has brought the CA 19-9 marker to 93 U/ml.

The patient was administered biweekly intradermal injections with concentrated Sendai virus strain STRS1 ($10^9$ I.E./ml) in 20 locations mixed with $10^7$ day 4 chicken embryo cells over a period of 9 months. CA 19-9 continued to fall during the next three months to 58.5 U/ml. Then a gradual increase in CA 19-9 was observed in the next three months to 308 U/ml then during one month to 940 U/ml. Over the next three weeks, CA 19-9 increased to 5962 U/ml then to 15888 U/ml (five weeks).

A virus cocktail containing STR4E1, STR11CB2, and STR14CB5 was injected biweekly intramuscularly over a period of two months. The following dynamics of CA 19-9 marker were observed: 16813 U/ml (after two weeks), 12944 U/ml (after four weeks), and 13121 U/ml (after six weeks). The figures indicate that the observed exponential rise in CA 19-9 stopped and even decreased somewhat. However, in the following weeks the process resumed—next two weeks—22876, next two weeks—following weeks, the process resumed: 22876 U/ml (after eight weeks), 34589 U/ml (after ten weeks), and 100345 U/ml (after twelve weeks). Fluid in the mediastinal region started to buildup. It was collected and inspected for tumor cells. The cells were seeded to cell culture and were propagated for further examination of their sensitivities to oncolytic viruses.

Example 22

Patient N. S., a 76 year old female, was diagnosed with colon carcinoma (sigmoidal) four years ago. The tumor was surgically removed with restoration of colonic connection to the rectum. Metastases to the liver and ileum were observed. The ileum was partially resected two years ago, and the patient was subjected to chemotherapy that stabilized the disease. One year ago, the patient was diagnosed with malignant melanoma and with metastases to retroperitoneal and inguinal lymph nodes. Taking into account the accompanying pathological conditions (severe atherosclerotic lesions in aorta, cardiosclerosis, and pulmonary emphysema), no chemotherapy was suggested.

The patient was administered biweekly intramuscular injections of oncolytic virus cocktail: Echovirus 7 strain STR6E7, Reovirus 1 strain STRR1, and Newcastle disease virus strain STRNH1 ($10^9$ I.E. each of the following strains). There was a strong temperature reaction lasting three days that was efficiently blocked by analgesics (ibuprofen and diclophenac). After three weeks ultrasonic examination revealed slight shrinking of retroperitoneal and inguinal lymph nodes.

Example 23

Patient S. E, a 42 year old female, was diagnosed with granulosa cell ovarian carcinoma with metastases to peritoneum. The tumor was surgically removed a year and a half ago. Histology examination confirmed granulosa cell carcinoma, adult type, T1aN×M0. Post surgery disease progression was observed, which included carcinomatosis of peritoneum and ascites.

Following surgery the patient underwent 5 courses of chemotherapy (3 months) that included 3 days cisplatine 100 mg, etoposide 200 mg No. 3; carboplatine 450 mg, and etoposide 200 mg No. 2. Post chemotherapy ultrasonic examination showed further progression of the disease. Large formations filled with liquid and partitioned with septums were observed in the left side of the small pelvis up to 51 mm; and in the right side up to 65 mm.

The chemotherapy scheme was changed to: four one-day courses of paclitaxel, 260 mg. Nevertheless, the disease worsened. Along the iliac vessels a voluminous formation was visualized with irregular cystoid ecostructure, 87 mm×57 mm, with blood supply along the septums. In the right retroperitoneal space, below the lower pole of the kidney—a similar voluminous cystic structure of 55 mm×35 mm was observed.

A third line of chemotherapy was applied: five courses of 3-day application of ifosfamidum 2 grams, MeSNa 2 grams, cisplatine 30 mg, etoposide and 150 mg. Chemotherapy appeared ineffective.

Oncolytic virus therapy was started one year after the surgery. The patient was subjected to weekly intradermal injections in the dorsum (near vertebrae) with STRS1 (oncolytic strain of Sendai virus) ($10^8$ IE) mixed in vitro with $2\times10^6$ day 5 chicken embryo fibroblasts. Reaction to the first administration was a temperature rise to 37.8° C. about 20 hours after the injections, which lasted for 10 hours. Reaction to the second administration was mild temperature rise (37.2° C.) lasting for 5-6 hours. Subsequent administrations had no reaction. The patient was subjected to oncolytic virus therapy for a period of 3 months.

Figure 7:
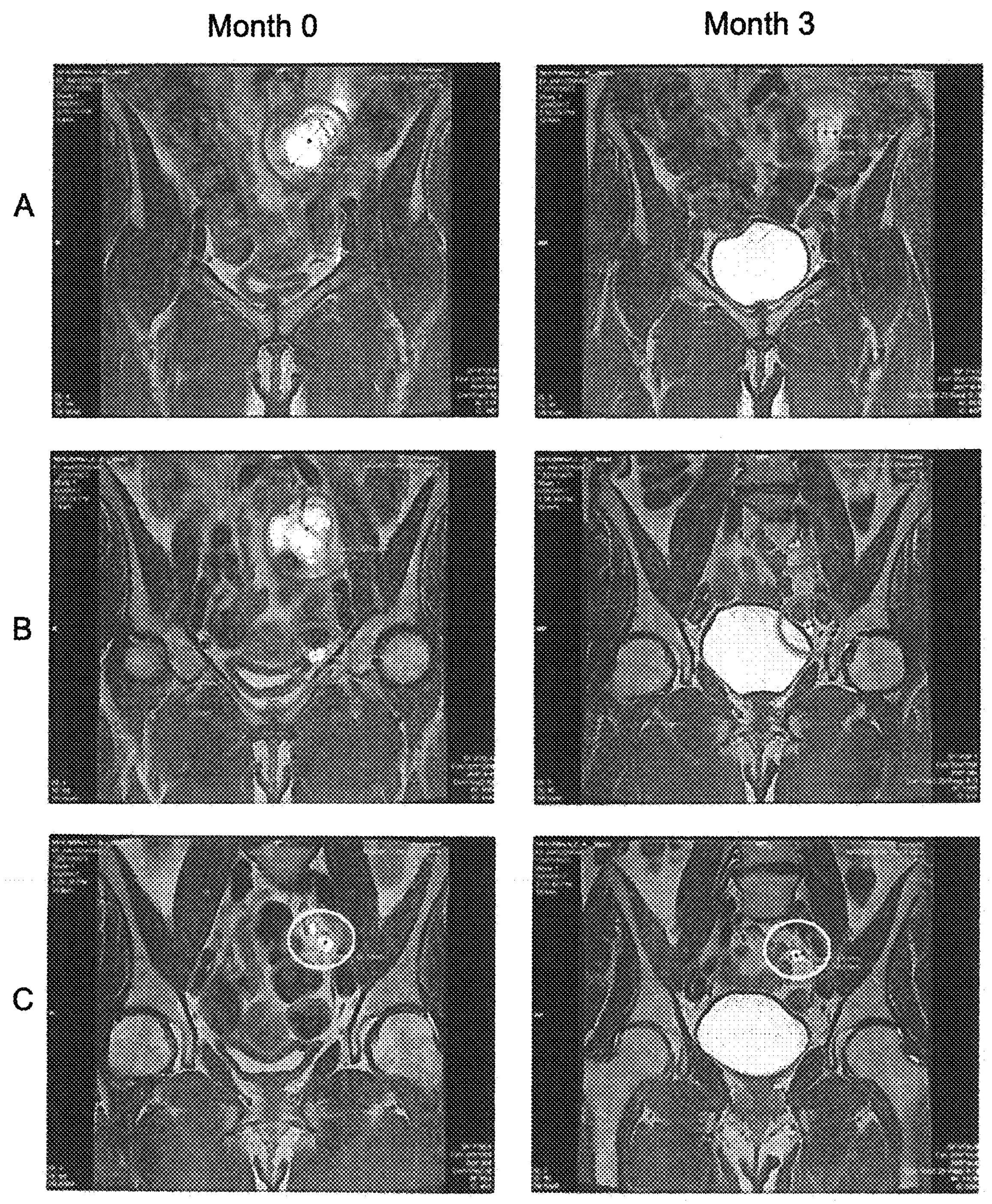
FIG. 7 is a set of six tomography scans that illustrate viral potency in humans. Sendai virus (STRS1) was applied to treat human granulosa cell ovarian carcinoma with metastases to the peritoneum of a 42 year-old female. The left column is a set of three tomography scans prior to viral treatment. Weekly intradermal injections of Sendai virus led to a substantial reduction in the tumor volume over a period of 3 months. The right column is a set of three tomography scans after the viral treatments. Tumor mass (including various metastatic nodes) is circled.

After viral therapy, ultrasonic examination showed signs of substantial improvement. No liquid in the peritoneal cavity was visible. Subsequent MR tomography showed substantial improvement with a reduction in a number of tumor nodes and their volume. See FIG. 7. Gadovist contrast no longer accumulated.

Example 24

Patient O. L., a 49 year old female, was diagnosed (two years ago) with diffuse astrocytoma of the brain, Grade II. A massive intraaxial tumor of the left frontal lobe was revealed.

Two years ago, the patient underwent an awake craniotomy for partial removal of the tumor. During surgery, the patient experienced focal and grand mal seizures which limited the ability to monitor language function. Electrophysiological monitoring for Motor Evoked Potentials (MEP) and motor functions were conducted throughout the operation. At some point when a decrease in MEP was observed and after decompression of the edematous brain, which was under severe pressure at the beginning of the operation, further resection was stopped and the operation concluded. Post-surgery the patient showed right hemiparesis with motor dysphasia, which improved after several hours when patient was put on high-dose steroids with mannitol infusions. Post-operative CT showed the partial resection cavity with no hemorrhage and severe edema similar to the pre-operative MRI images. Several days after surgery the patient deteriorated, and became stuporous and less communicative. Steroid dose was increased as well as the frequency of mannitol infusion with control of sodium levels. The prognosis appeared grim.

Post-surgery, the patient was subjected to a course of remote conformal radiation therapy (30 sessions of 2 Gy; total 60 Gy). Condition slightly improved.

The patient was subsequently subjected to 6 courses of chemotherapy with Temozolomide (250 mg). The overall dynamics were found to be negative. CT scan showed increased accumulation of contrasting matter in the brain. Thirteen months ago, a chemotherapy course with temodal was repeated, again with no substantial improvement.

A year ago, oncolytic virus therapy started. Reovirus 1 strain (STRR1) was injected intramuscularly $10^9$ IE. The initial reaction included minor Intestinal discomfort and a very mild temperature rise (37.2° C.-37.5° C.) lasting for a few hours. Subsequent administrations continued for one month with no adverse reactions. MRI showed small positive dynamics.

STR4E1 (Echovirus 1) was applied weekly (intramuscularly $10^9$ IE) for one month. No adverse reaction was observed.

STR14CB5 (Coxsackievirus B5) was then applied weekly (intramuscularly $10^9$ IE) for one month. Fatigue and dizziness resulted during the first application. There were no adverse reactions during the second application. Brain MRI showed stabilization of the disease. Moderate positive dynamics were observed.

Weekly intramuscular injections of STR14CB5 (Coxsackievirus B5) $10^9$ IE continued for two more weeks. No adverse reactions were observed. MRI and PET/CT showed positive dynamics in the form of reducing the size of the sections of contrast.

STR8CA7 (Coxsackievirus A7) was the applied weekly intramuscularly $10^8$ IE for 3 weeks. Minor fatigue was observed after the first injection on the next day. Second and third injections led to no adverse reactions.

Figure 8:
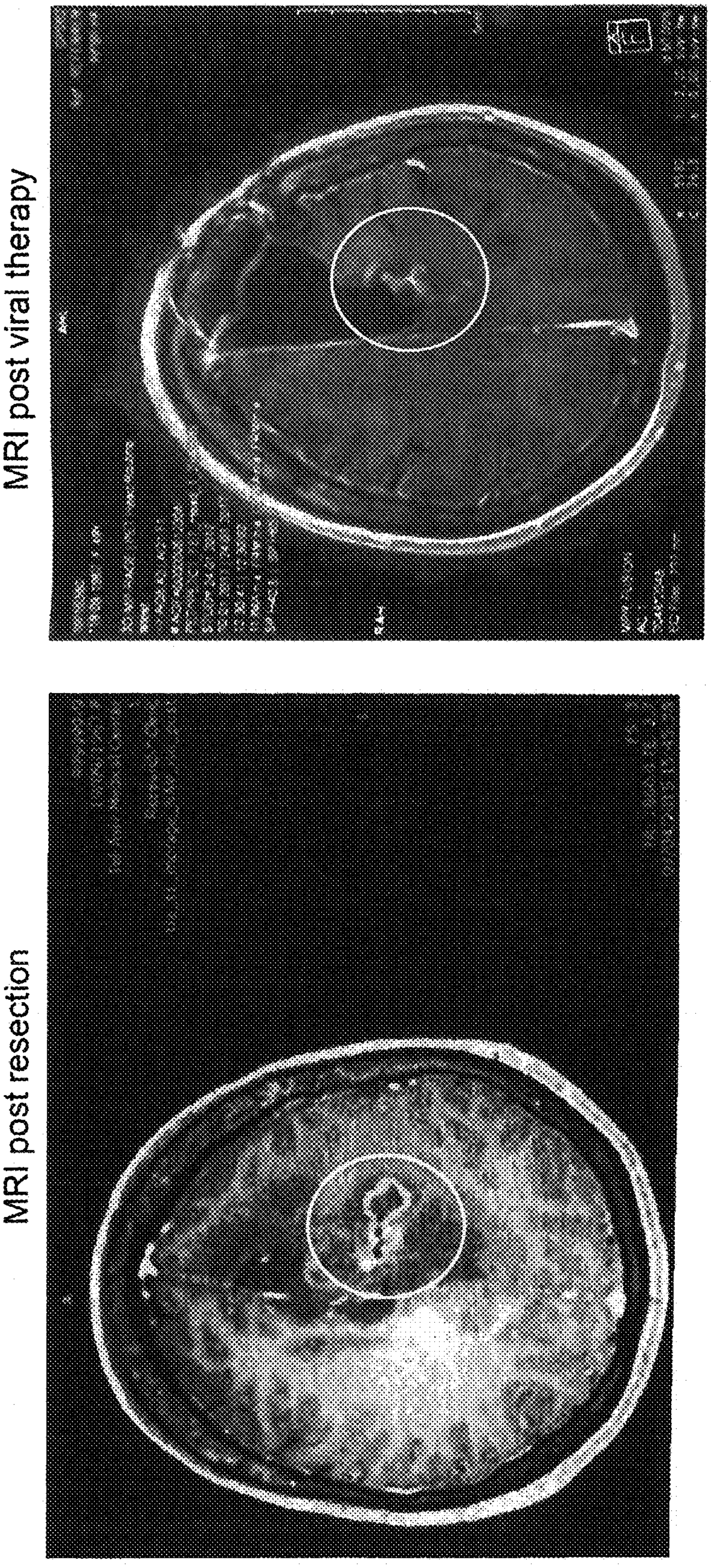
FIG. 8 is a set of two magnetic resonance imaging (MRI) pictures that illustrate viral potency in humans. Several courses of Reovirus 1, intramuscularly $10^9$ IE; Echovirus 1, intramuscularly $10^9$ IE; Coxsackievirus B5 intramuscularly $10^9$ IE; Coxsackievirus A7 intramuscularly $10^8$ IE; and Poliovirus strain 1 intramuscularly $10^8$ IE were applied to treat diffuse astrocytoma of the brain with massive intraaxial tumor of the left frontal lobe of a 49 year-old female Patient. The patient underwent subtotal resection of the left frontal lobe, but the tumor could not be completely resected, as tumor growth was too close to the vital parts of the brain. Following one course of radiotherapy and several courses of chemotherapy the tumor increased in size. Weekly intramuscular injections of oncolytic viruses led to a substantial reduction in the tumor volume over a period of 4 months. The left image is an MRI post resection and before viral therapy. The right image is an MRI after viral therapy was administered. The tumor nodes are circled.

Poliovirus 1 (Sabin strain) $10^8$ IE intramuscular was then applied weekly for two weeks. Minor chills were observed the next day after the first injection. No adverse reactions occurred after the second administration. MRI showed further positive dynamics in the form of reduction in the size of the contrasting areas (FIG. 8).

Poliovirus 1 (Sabin strain) $10^8$ IE intramuscular injections continued. No adverse reactions occurred. The patient's condition substantially improved. The patient communicates almost normally, is more arousable, and walks 2-3 hours every day.

Example 25

Patient N. D., a 59 year old male, was diagnosed (three years ago) with pancreatic ductal adenocarcinoma localized in the pancreas body. Ultrasonic examination showed a tumor in the body of the pancreas—44 mm×35 mm, stenosis of superior mesenteric artery and celiac trunk, splenomegaly. A19-9 tumor marker levels were 125 U/ml, CEA levels were 5 ng/ml. Laparoscope-assisted puncture of the tumor for biopsy resulted in A19-9 marker increase to 512 U/ml. A year later, CA19-9 tumor marker increased to 2338 U/ml and then (four months later) to 4557 U/ml. Jaundice developed because of the obstruction of choledochus. A stent was introduced to treat the condition. CA19-9=7416 U/ml.

Oncolytic virus therapy was started using STRS1 (oncolytic strain of Sendai virus) ($10^8$ IE). The patient was subjected to 16 weekly intradermal injections with STRS1 in the dorsum, near vertebrae. Reaction to the first administration was a temperature rise to 37.8° C.-38° C. (manageable with aspirin) lasting for 4 hours. Follow up administrations had no adverse reactions.

Ultrasonic examination four months post-viral treatment showed a reduction in tumor volume from 45 mm×38 mm to 42 mm×32 mm, and a decrease in the amount of the free fluid in the abdomen and overall positive dynamics. CA19-9 marker levels were 2878 U/ml.

A cocktail of three viruses, STR4E1 (Echovirus 1 ($2×10^8$ I.E./ml)), STRR1 (Reovirus 1 ($5×10^7$ I.E./ml)), and STR8CA7 (Coxsackievirus A7) ($10^8$ I.E./ml), was applied by intramuscular injection. Fever developed 14 hours after the injection. Temperature increased to 38.5° C. and remained elevated for 4-5 hours (no aspirin taken), and then dropped to 37.2° C.-37.4° C. and stayed at this level during the next 24 hours. Fatigue was experienced during the following three days. Injection of the cocktail of three viruses was repeated. The reaction was a mild temperature (37.5° C.) lasting for 5 hours. Condition stabilized, positive dynamics were observed. CA19-9 marker levels were 1316 U/ml.

Example 26

Patient I. V., 39 year old female, was diagnosed (six years ago) with triple negative breast carcinoma (right breast), T2N0M0, malignant Grade 3, Invasive basal-cell phenotype. The patient underwent radical sectorial resection of the right breast and regional lymph nodes. The patient was subjected to six courses of adjuvant chemotherapy: Docetaxel+Doxorubicin and then radio (gamma) therapy. The disease progressed, with metastases to left lung, thyroid gland, liver (left lobe) and left adrenal gland. The patient was subjected to an additional six courses of chemotherapy: Bevacizumab 840 mg, Carboplatine AUC 6, once every 3 weeks plus weekly injections of paclitaxel (120 mg). Partial remission was initially observed, followed by overall negative dynamics.

Two years ago, oncolytic virus therapy started using STRS1 (Sendai virus). 16 intradermal injections were applied in the dorsum, near the vertebrae. Two months later, Computer Tomography showed positive dynamics. The nodule in the lung shrunk from 19 mm×20 mm to 10 mm×15 mm. Focal calcification of the tumor was observed, and formation of an air-filled structure (17 mm) near the tumor was also observed.

STRS1 treatment continued, but was followed by negative dynamics. An increase in size of the lung metastasis to 60 mm×46 mm×55 mm was observed. Accumulation of ascites, metastases to pelvis region, to ovary, uterus and penetration to bladder was also noted, along with enlargement of retroperitoneal lymph nodes.

Ascites fluid (830 ml) was taken for examination. The liquid contained spheroid aggregates of tumor cells ($1$-$1.5×10^5$ cells/ml). The whole collected volume of ascites fluid was centrifuged to collect tumor cells. The cells were washed with DMEM and frozen in liquid nitrogen in 50% FCS, 10% DMSO for further testing for virus sensitivity.

Cancer cells were tested for virus sensitivity. They appeared to be sensitive to STRS1 (Sendai virus), however ascites fluid was found to contain high titer of anti-STRS1/neutralizing antibodies. Cancer cells were further tested and appeared to be sensitive to STRNH1 (Newcastle disease virus, H-strain), STR4E1 (Echovirus 1), Sabin strains of Polioviruses (1,2,3 types) and STR14CB5 (Coxsackevirus B5). These cells also showed moderate sensitivity to STR15CB6 (Coxsackievirus B6) and appeared to be not sensitive to STR8CA7 (Coxsackievirus A7) and STR17E21 (Echovirus 12).

The patient was subjected to intraperitoneal administration of $2×10^8$ I.E. STR4E1 (Echovirus 1). The body temperature increased 16 hours after the administration to 38.5° C. (managed by aspirin), and returned to normal within the next 24 hours. Ascites fluid volume decreased substantially. The overall condition of the patient improved.

Treatment continued with intravenous injections of $2×10^8$ I.E. STR4E1 (Echovirus 1) in 200 ml, 40 minutes perfusion (weekly for 7 weeks). Computer Tomography showed signs of substantial positive dynamics. Lung metastasis shrank to 26 mm×19 mm×21 mm, retroperitoneal lymph nodes diminished in size to 4-5 mm, no ascites in abdominal cavity was observed, and the tumor mass diminished in the pelvis to 38 mm×41 mm×48 mm.

Treatment continued with two courses of intramuscular injection of STR14CB5 (Coxsackievirus B5) $1×10^8$ I.E. and two courses of intravenous injections of STR14CB5 (Coxsackievirus B5) $2×10^8$ I.E. in 200 ml, 40 minute perfusion. Computer Tomography showed substantial positive dynamics. Lung metastases diminished to 15 mm×10 mm, retroperitoneal nodes became not visible in the CT. Tumor masses in the pelvis reduced to 16 mm×17 mm. Condition is stable.

Example 27

Patient T. D., 39 year old female, was diagnosed (three years ago) with colon adenocarcinoma localized in the region of left bend, T4N2bM0. The patient underwent laparoscopy-assisted left-side hemicolectomia followed by eight courses of adjuvant chemotherapy (FOLFOX scheme), which were ineffective. Disease progressed. Metabolically active tumor tissues were found both in the region of the primary tumor as well as further in the pancreas tail and left kidney. Metastases were spread to left ovary, carcinomatosis of peritoneum and ascites developed.

A year ago, 200 ml of ascites fluid was collected (cell count ~$4\times10^4$ cells/ml), tumor cells isolated and tested for sensitivity to viruses. Tumor cells appeared to be highly sensitive to Sabin strains of Polioviruses (1,2,3 types), STR6E7 (Echovirus 7) and STR7E12 (Echovirus 12), STR15CB6 (Coxsackievirus B6), STRNH1 (Newcastle disease virus, strain H), and Measles virus (Edmonston vaccine strain); moderately sensitive to: STR14CB5 (Coxackievirus B5), STRS1 (Sendai virus) and STR8CA7 (Coxsackievirus A7); and had low sensitivity to STR4E1 (Echovirus 1), STRR1 (Reovirus 1) and STRR2 (Reovirus 2).

At the same time (a year ago), the patient underwent a follow-up surgery, i.e. removal of the recurrent tumor, resection of left kidney and adrenal gland, distal resection of pancreas, resection of spleen, resection of both Fallopean tubes and ovaries, and resection of greater omentum. The surgery was followed by nine courses of XELOX chemotherapy that was applied as follows: once in 21 days, oxaliplatine 120 mg/$m^2$ and capecitabine 2000 mg/$m^2$ orally at days 1 and 14. The chemotherapy was poorly tolerated, with signs of neuropathy and substantial emetic reactions. Disease progressed.

Six months ago, viral therapy started with intramuscular injection of a mixture of STR7E12 (Echovirus 12) and STR15CB6 (Coxsackievirus B6), $2\times10^8$ I.E. each. Reaction was a temperature increase (37.5° C.-38.0° C.) 22 hours after the injection, some headache and chills (lasted for 2-3 hours, both were curtailed by aspirin and ibuprofen). A more aggressive treatment protocol with intravenous administration of viruses twice a week for 7 weeks STR7E12 (Echovirus 12) and STR15CB6 (Coxsackievirus B6), $2\times10^8$ I.E. i.v. perfusion in 200 ml for 20 minutes was then followed.

Multispiral computer tomography examination was performed after one month of viral therapy. Chest: C2, right lung, few foci of 7, 10, 12 mm, less clear contours compared with previous examination before virus treatment. C6, right lung—8 mm; Left lung, paraortal in upper lobe (C3-up to C1) 14 mm×15 mm, with no dynamics. Visible normalization of lung tissue pattern (formerly it was intensified) and some reduction in size of formerly seen foci—C2, right—from 4 mm to 2 mm, C10—as a fibrous stretch; other foci are not clearly visible. No formation of new foci. The lung's volume was preserved, lung area was symmetrical, and the trachea and bronchi were not obstructed and were not deformed. No free liquid was found in the pleural region, and the pleura was of normal thickness. A small accumulation of liquid in the pericardial lumen, near the apex cardia, was revealed. Mediastinum was of normal structure. In the mediastinum and in the roots of lungs, solitary lymph nodes up to 8 mm were found. All groups of lymph nodes were diminished in size to virtually normal values. In the abdomen, the liver was of normal size, with a smooth and clear contour. In C2, C4, C5, C6, small hypodensive foci with density of liquid, clear contoured, up to 10 mm, were located. They did not accumulate a contrasting substance, no dynamics, and no formation of new foci. In C7 in the liver in arterial and venous phases a hypodensive zone was visible, with uneven contour up to 4-6 mm, no dynamics, no new foci. Intra- and para-hepatic biliar vessels were not dilated. The gall bladder had an even contour and walls of normal thickness. An even round-shaped formation with a hypodensive center, 15 mm, was seen in the region of parapancreatic tissue, showing no dynamics except a more pronounced hypodensive center. No ascites was found in the abdominal region. Lymph nodes in the region of small curve of the stomach were up to 8 mm (diminished) and in the liver gates were up to 10 mm (diminished). The conclusion was that viral therapy resulted in stabilization and positive dynamics.

Viral therapy continued. A cocktail of Poliovirus 1 (Sabin strain) and STR6E7 (Echovirus 7), $2\times10^8$ I.E, i.m. injections (weekly) was applied. The reaction to this cocktail was some chills, fatigue, a temperature increase to 37.2° C.-37.6° C. after the first administration. Condition further improved. The patient is stable.

Veterinary Use of STRS

Malignant diseases are the major causes of deaths of old age dogs and cats. Some of the oncolytic viruses from the tested panel can efficiently infect cells of dog and cat origin. These oncolytic viruses include Sendai virus strain STRS1, Newcastle disease virus strain STRNH1, Canine distemper virus strain STRCDV1 (developed based on a live CDV vaccine strain), reoviruses Type 1, 2 and 3 STRR1, STRR2, and STRR3. These strains were tested in a veterinary clinic for the treatment of domestic cats and dogs.

Mast cell carcinoma is one of the most common and deadliest tumors in dogs. Tumors can be localized subcutaneously and are easily accessible by surgery. However, after surgical removal, they tend to result in very aggressively growing metastases, both in the region of the primary tumor and distantly.

To test whether oncolytic viruses could be used for the treatment STRS1 and STRR1 oncolytic viruses were utilized.

Example 28

Hersh, a 13 year old Poodle, was diagnosed with mastocytoma in the region of front paw. The tumor was rapidly growing (from the size of 5 mm×5 mm to 25 mm×30 mm over three weeks). The tumor was surgically removed. Starting on day 14, malignant tumor growth was detected in the region of the surgical suture. The tumor region was injected subcutaneously with concentrated STRS1, with intervals of 5 min. A total of 15 injections, 0.2 ml each ($2\times10^8$ I.E. per ml), was administered. Tumor growth stopped, and by day 14, there were no visible traces of tumor masses. The suture efficiently healed with no further growth of the tumor over the next 8 months.

Example 29

Istra, an 11 year old Shar Pei, was diagnosed with mastocytoma in the left hind region. The tumor was rapidly growing (34 mm×56 mm), and no surgery was considered. The tumor was injected in 10 different regions with 2 ml of STRS1. Surrounding skin was also injected with STRS1 (0.2 ml per injection) for a total of 12 injections. There was swelling of the tumor two days after injections. The swelling subsided 10 days after the injections. There was no substantial reduction of tumor size, but the tumor stopped its growth. Four months after the injection, the tumor was resected and examined. The tissue contained mostly regions of fibrosis with some atypical rounded cells. No relapses of tumor growth were observed during the following five months.

Example 30

Twenty-seven cases of mast cell carcinoma in dogs were observed. After the initial experience with mast cell tumors in dogs, a few other cases of mast cell tumor were observed to which treatment with STRS1 was applied. Out of the total of 27 cases of mast cell carcinomas, 15 cases exhibited stable relapse-free cure of the disease for over one year following three biweekly injections of STRS1. Five dogs represented terminal cases with systemic spread of tumor cells, in which the owners eventually decided on euthanasia. Seven cases for long-term evaluation were untraceable.

Example 31

Fourteen cases of mast cell carcinoma in cats were observed. Ten cases represented mast cell tumors localized subcutaneously, and four cases were terminal stages with systemic spread of the tumor. In cases of localized tumors, the tumors and the surrounding regions were injected three times with concentrated STRS1 every two weeks. Eight cats from the group had a positive response with no further progression of the disease for at least six months. Two cats did not respond to the treatment and perished. Of the four cases with systemic spread of mast cell tumors, two had partial responses with recurrent growth during the following two months. Of these, one cat (8 year old female) was injected with STRR1 into all six visible tumors. Tumor growth stopped for at least one month. The fate of the cat is unknown.

Example 32

Jack, a 14 year old Terrier, was diagnosed with osteosarcoma of the right rear limb, which was removed. Recurrent growth was observed one month after the surgery. The tumor site was injected with 5 ml of concentrated STRS1. In total, five injections infiltrated the site around the tumor. There was swelling of the limb lasting for three days with an apparent local rise in temperature. Ultrasonic examination three weeks after the injection revealed stabilization of the process and some shrinking of the tumor. Tumor growth resumed 64 days after the injection. The tumor region was injected with 5 ml concentrated STRR1 ($2\times10^8$ I.E. per ml). There was again swelling of the limb lasting for three days. Ultrasonic examination two weeks after the injection revealed a stabilization of the process. There was no relapse for the next two months.

Example 33

Mura, a 9 year old cat, was diagnosed with mammary carcinoma with local spreading, which was surgically removed. Recurrent growth was observed two months after the surgery. The region of the tumor was injected with concentrated virus cocktail containing STRS1, STRNH1 and STRR1. There was local swelling lasting for one week. Tumor growth stopped, and there was no relapse for at least two months.

Discussion

Broadly, Coxsackievirus A7/STR8CA7; Coxsackievirus B5/STR14CB5; and Coxsackievirus B6/STR15CB6 have shown a positive therapeutic effect on tumor growth.

As shown in FIGS. 1A-1C, viruses that replicate poorly do not show oncolytic activity in xenograft tumors derived from the same cells in nude mice. In contrast, viruses that display strong replication activity in xenograft tumors are capable of destroying xenograft tumors. Namely, as seen in FIG. 1A, the application of Coxsackievirus A7/STR8CA7 to xenograft tumors of C33A cells resulted in significantly smaller tumor volumes over a period of 50 days than either the control (C33A cells alone) or Coxsackievirus B3 applied to C33A cells. Similarly, as seen in FIG. 1B, the application of Coxsackievirus B4 to xenograft tumors of AsPC1 cells resulted in significantly smaller tumor volumes over a period of 50 days than either the control (AsPC1 cells alone) or Coxsackievirus A7 applied to AsPC1 cells. Further, as shown in FIG. 1C, Echovirus 1 has shown greater efficacy when applied to MCF7 cells than either the control (MCF7 cells alone) or Coxsackievirus B6/STR15CB6 applied to MCF7 cells.

These results indicate that specific viruses have specific effects depending on the type of cell/tumor to which the viruses are administered, indicating there is a need to determine patient specific sensitivity so as to determine what viruses should be administered.

Patient specific sensitivity may be a measurement taken on a comparison basis. Tumor samples displaying sensitivity to a particular human virus may produce up to $10^6$-$10^7$ TCID50 per ml. However, one virus may show greater TCID50 per ml than another virus, indicating a greater sensitivity to one virus. Such a comparison provides a means not only for selecting what types of single viruses may be selected but if they may be used in a panel of viruses.

As discussed above, panels of viruses may be administered sequentially or simultaneously. The efficiency of simultaneous use of virus mixtures is demonstrated in xenograft experiments in nude mice bearing tumors derived from the C33A human cervical carcinoma cell line and injected with single viruses displaying different propagation capacities in the cells and mixtures of two or three viruses (FIG. 2). As shown, the most effective panel on A431 cells was that of Echovirus 12 with Coxsackievirus B5 and CoxsackievirusB6. Indeed, these oncolytic viruses demonstrated an added effect on A431 cells. Echovirus 12 resulted in the single most therapeutic effect with respect to retarding tumor volume over 50 days; however, this effect was compounded with the addition of the Coxsackieviruses, which also showed a compounded effect compared to Coxsackievirus B5 and Coxsackievirus B6 alone.

The above-disclosed examples also indicated that bioselecting viruses and inducing mutagenesis might result in viruses that do not cross-neutralize with antiserums. Such a technique could also be applied so as bioselect oncolytic viruses that would a) not interact with one another and b) would not interact with other cancer therapies, such as chemotherapy, radiation, drug therapy, etc.

The manufacture of synthetic/systemic targeted remedies (STRs) has resulted in effective tumor treatments in both humans and animals. Regarding application of oncolytic viruses in humans, the effects of the administered viruses were tumor specific. For example, adenocarcinoma of urachus was highly susceptible to STRS1, STRR1, STRMESC1, STR4E1, STR7E12, STR14CB5, STR15CB6, and resistant to STR8CA7. However, prostate acinar adenocarcinoma showed susceptibility to Sendai virus strain STRS1 alone, thereby indicating the criticality of selecting patient and cancer specific oncolytic viruses for the most effective treatments.

With respect to veterinary applications, STRS1 and STRR1 showed significant efficacy reducing tumor growth and relapse. Biweekly injections in both dogs and cats resulted in severely reduced tumor masses as well as the formation of fibrosis (scar tissue).

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method of treating a cancer patient, comprising:

administering to the patient a first composition containing an effective amount of at least a first natural oncolytic virus for a first time period; and administering to the patient a second composition containing an effective amount of at least a second natural oncolytic virus that is different from the first oncolytic virus for a second time period;

wherein the second composition is administered between one week to 24 weeks after the first composition is administered; and wherein a tumor volume in the cancer patient is reduced after the first composition and the second composition are administered wherein the first natural oncolytic virus is an echovirus, a coxsackievirus, or a poliovirus;

wherein the second natural oncolytic virus is an echovirus, a coxsackievirus, or a poliovirus; and wherein either the first natural oncolytic virus or the second natural oncolytic virus is an echovirus.

2. The method of claim 1, wherein the first composition is administered multiple times during the first time period; and wherein the second composition is administered multiple times during the second time period.

3. The method of claim 1, wherein the first and second compositions are administered orally, nasally, intravenously, intra-arterially, intravaginally, intraurethrally, intratumorally, intracranially, intra spinally, or by means of a cellular carrier infected with the first or second oncolytic virus in vitro.

4. The method of claim 1, where in the first and second natural oncolytic viruses differ in their host-cell surface receptor required for cell entry; and wherein the host-cell surface receptor required for cell entry is CD155, integrin α2β1, integrin αVβ3, integrin αVβ6, ICAM-1, CD55, CXADR, CD46, JAM-1, PVRL1, PVRL4, CD150, L-SIGN, VLDVR, NRAMP2, sialic acid, PGSL-1 (aka CD162), SCRAB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparin sulfate.

5. The method of claim 1, wherein the first and second compositions each contain a plurality of natural oncolytic viruses.

6. A method of treating a cancer patient, comprising:

administering to the patient a first composition containing an effective amount of at least a first natural oncolytic virus and a second natural oncolytic virus for a first time period, wherein the first and second natural oncolytic viruses differ in their host-cell surface receptor required for cell entry; and wherein a tumor volume in the cancer patient is reduced after the first composition is administered;

wherein the first natural oncolytic virus and the second natural oncolytic virus are independently an echovirus, a coxsackievirus, or a poliovirus.

7. The method of claim 6, wherein the first and second natural oncolytic viruses are each present in a dosage of about $1\times10^4$ TCID50 to about $1\times10^{11}$ TCID50.

8. The method of claim 6, wherein the host-cell surface receptor required for cell entry of the first natural oncolytic virus and a second natural oncolytic virus is independently selected from CD155, integrin α2β1, integrin αVβ3, integrin αVβ6, ICAM-1, CD55, CXADR, CD46, JAM-1, PVRL1, PVRL4, CD150, L-SIGN, VLDVR, NRAMP2, sialic acid, PGSL-1 (aka CD162), SCARB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparin sulfate.

9. The method of claim 1, wherein the first and second natural oncolytic viruses are present in a dosage of about $1\times10^4$ TCID50 to about $1\times10^{11}$ TCID50.

10. The method of claim 1, further comprising:

prior to administering the first composition and the second composition, testing the patient's malignant cells to identify the first natural oncolytic virus and the second natural oncolytic virus.

11. The method of claim 1, wherein the second composition is also administered after neutralizing antibodies against the first natural oncolytic virus have been induced.

12. The method of claim 6, wherein the second composition is also administered after neutralizing antibodies against the first natural oncolytic virus have been induced.

13. The method of claim 1, wherein the first natural oncolytic virus is echovirus 1, and the second natural oncolytic virus is Coxsackievirus B5.

14. The method of claim 6, wherein the first natural oncolytic virus is echovirus 12, the second natural oncolytic virus is Coxsackievirus B5, and further comprising a third natural oncolytic virus which is Coxsackievirus B6.

15. The method of claim 6, wherein the first natural oncolytic virus is echovirus 1, and the second natural oncolytic virus is Coxsackievirus A7, and further comprising a third natural oncolytic virus which is Coxsackievirus B5.

16. The method of claim 6, wherein the first natural oncolytic virus is echovirus 12, and the second natural oncolytic virus is Coxsackievirus B6; and further comprising administering to the patient a second composition containing an effective amount of poliovirus 1 and echovirus 7 for a second time period;

wherein the second composition is administered between one week to 24 weeks after the first composition is administered.

* * * * *

SEQUENCE LISTING

```
<160> NUMBER OF SEQ ID NOS: 2

<210> SEQ ID NO 1
<211> LENGTH: 6630
<212> TYPE: DNA
<213> ORGANISM: Poliovirus Sabin strain Type 1

<400> SEQUENCE: 1

atgggtgctc aggtttcatc acagaaagtg ggcgcacatg aaaactcaaa tagagcgtat      60

ggtggttcta ccattaatta caccaccatt aattattata gagattcagc tagtaacgcg     120

gcttcgaaac aggacttctc tcaagaccct tccaagttca ccgagcccat caaggatgtc     180

ctgataaaaa catccccaat gctaaactcg ccaaacatag aggcttgcgg gtatagcgat     240

agagtactgc aattaacact gggaaactcc actataacca cacaggaggc ggctaattca     300

gtagtcgctt atgggcgttg gcctgaatat ctgagggaca gcgaagccaa tccagtggac     360

cagccgacag aaccagacgt cgctgcatgc aggttttata cgctagacac cgtgtcttgg     420

acgaaagagt cgcgagggtg gtggtggaag ttgcctgatg cactgcggga catgggactc     480

tttggccaaa atatgtacta ccactaccta ggtaggtccg ggtacaccgt gcatgtacag     540

tgtaacgcct ccaaattcca ccagggggca ctaggggtat tcgccgtacc agagatgtgt     600

ctggccgggg atagcaacac cactaccatg cacaccagct atcaaaatgc caatcctggc     660

gagaaaggag gcactttcac gggtacgttc actcctgacg acaaccagac atcacctgcc     720

cgtaggttct gcccggtgga ttacctcttt ggaaatggca cgttattggg gaatgccttt     780

gtgttcccgc accagataat aaacctacgg accaacaact gtgctacact ggtactccct     840

tacgtgaact ccctctcgat agatagtatg gtaaagcaca ataattgggg aattgcaata     900

ttaccattgg ccccattaaa ttttgctagt gagtcctccc cagagattcc aatcaccttg     960

accatagccc ctatgtgctg tgagttcaat ggattaagaa acattaccct gccacgctta    1020

cagggcctgc cggtcatgaa cacccctggt agcaatcaat atcttactgc agacaacttc    1080

cagtcaccgt gtgcgctgcc tgaatttgat gtgaccccac ctattgacat acccggtgaa    1140

gttaagaaca tgatggaatt ggcagaaatc gacaccatga ttccctttga cttaagtgca    1200

aaaaaaaaga acaccatgga aatgtatagg gttcggttaa gtgacaaacc acatacagac    1260

gatcccatac tctgcctgtc actctctcca gcttcagatc ctaggttgtc acatactatg    1320

cttggagaaa tcctaaatta ctacacacac tgggcaggat ccctgaagtt cacgtttctg    1380

ttctgtggat ccatgatggc aactggcaaa ctgttggtgt catacgcgcc tcctggagcc    1440

gacccaccaa agaagcgtaa ggaggcgatg ttgggaacac atgtgatctg ggacatagga    1500

ctgcagtcct catgtactat ggtagtgcca tggattagca acaccacgta tcggcaaacc    1560

atagatgata gtttcaccga aggcggatac atcagcgtct tctaccaaac cagaatagtc    1620

gtccctcttt cgacacccag agagatggac atccttggtt ttgtgtcagc gtgtaatgac    1680

ttcagcgtgc gcttgatgcg agataccaca catatagagc aaaaagcgct agcacagggg    1740

ttaggtcaga tgcttgaaag catgattgac aacacagtcc gtgaaacggt gggggcggca    1800

acgtctagag acgctctccc aaacactgaa gccagtggac cagcacactc caaggaaatt    1860

ccggcactca ccgcagtgga aactggggcc acaaatccac tagtcccttc tgatacagtg    1920
```

-continued

```
caaaccagac atgttgtaca acataggtca aggtcagagt ctagcataga gtctttcttc   1980
gcgcggggtg catgcgtggc cattataacc gtggataact cagcttccac caagaataag   2040
gataagctat ttacagtgtg gaagatcact tataaagata ctgtccagtt acggaggaaa   2100
ttggagttct tcacctattc tagatttgat atggaattta cctttgtggt tactgcaaat   2160
ttcactgaga ctaacaatgg gcatgcctta aatcaagtgt accaaattat gtacgtacca   2220
ccaggcgctc cagtgcccga gaaatgggac gactacacat ggcaaacctc atcaaatcca   2280
tcaatctttt acacctacgg aacagctcca gcccggatct cggtaccgta tgttggtatt   2340
tcgaacgcct attcacactt ttacgacggt ttttccaaag taccactgaa ggaccagtcg   2400
gcagcactag gtgactccct ctatggtgca gcatctctaa atgacttcgg tattttggct   2460
gttagagtag tcaatgatca caacccgacc aaggtcacct ccaaaatcag agtgtatcta   2520
aaacccaaac acatcagagt ctggtgcccg cgtccaccga gggcagtggc gtactacggc   2580
cctggagtgg attacaagga tggtacgctt acacccctct ccaccaagga tctgaccaca   2640
tatggattcg gacaccaaaa caaagcggtg tacactgcag gttacaaaat ttgcaactac   2700
catttggcca ctcaggaaga tttgcaaaac gcagtgaacg tcatgtggaa tagagacctc   2760
ttagtcacag aatcaagagc ccagggcacc gattcaatcg caaggtgcaa ttgcaacgca   2820
ggggtgtact actgcgagtc tagaaggaaa tactacccag tatccttcgt tggcccaacg   2880
ttccagtaca tggaggctaa taactattac ccagctaggt accagtccca tatgctcatt   2940
ggccatggat tcgcatctcc aggggattgt ggtggcatac tcagatgtca ccacggggtg   3000
atagggatca ttactgctgg tggagaaggg ttggttgcat ttacagacat tagagacttg   3060
tatgcctacg aagaagaagc catggaacaa ggcatcacca attacataga gtcacttggg   3120
gccgcatttg gaagtggatt tactcagcag attggagaca aaataacaga gttgactaat   3180
atggtgacca gtaccatcac tgaaaagcta cttaagaact tgatcaagat catatcctca   3240
ctagttatta taactaggaa ttatgaagac accacaacag tgctcgctac cctggccctt   3300
cttgggtgtg atgcttcacc atggcagtgg cttagaaaga aagcatgcga tgttctggag   3360
ataccttatg tcaccaagca aggtgacagt tggttgaaga agtttactga agcatgcaac   3420
gcagctaagg gactggagtg ggtgtcaaac aaaatctcaa aattcattga ttggctcaag   3480
gagaaaatta tcccacaagc tagagataag ttggaatttg taacaaaact tagacaacta   3540
gaaatgctgg aaaaccaaat ctcaactata caccaatcat gccctagtca ggaacaccag   3600
gaaattctat tcaataatgt cagatggtta tccatccagt ctaagaggtt tgcccctctt   3660
tacgcagtgg aagccaaaag aatacagaaa ctagagcata ccattaacaa ctacatacag   3720
ttcaagagca aacaccgtat tgaaccagta tgtttgctag tacatggcag ccccggaaca   3780
ggtaaatctg tagcaaccaa cctgattgct agagccatag ctgaaagaga aaacacgtcc   3840
acgtactcgc taccccccgga tccatcacac ttcgacggat acaaacaaca gggagtggtg   3900
attatggacg acctgaatca aaacccagat ggtgcggaca tgaagctgtt ctgtcagatg   3960
gtatcaacag tggagtttat accacccatg gcatccctgg aggagaaagg aatcctgttt   4020
acttcaaatt acgttctagc atccacgaac tcaagcagaa tttccccccc cactgtggca   4080
cacagtgatg cattagccag gcgctttgcg ttcgacatgg acattcaggt catgaatgag   4140
tattctagag atgggaaatt gaacatggcc atggctactg aaatgtgtaa gaactgtcac   4200
caaccagcaa actttaagag atgctgtcct ttagtgtgtg gtaaggcaat tcaattaatg   4260
gacaaatctt ccagagttag atacagtatt gaccagatca ctacaatgat tatcaatgag   4320
```

-continued

```
agaaacagaa gatccaacat tggcaattgt atggaggctt tgttccaagg accactccag   4380
tataaagact tgaagattga catcaagacg agtccccctc ctgaatgtat caatgacttg   4440
ctccaagcag ttgactccca ggaggtgaga gattactgtg agaagaaggg ttggatagtc   4500
aacatcacca gccaggttca aacagaaagg aacatcaaca gggcaatgac aattctacaa   4560
gcggtgacaa ccttcgccgc agtggctgga gttgtctatg tcatgtataa actgtttgct   4620
ggacaccagg gagcatacac tggtttacca aacaaaaaac ccaacgtgcc caccattagg   4680
acagcaaagg tacaagggcc agggttcgat tacgcagtgg ctatggctaa aagaaacatt   4740
gttacagcaa ctactagcaa gggagagttc actatgttag gagtccacga caacgtggct   4800
attttaccaa cccacgcttc acctggtgaa agcattgtga tcgatggcaa agaagtggag   4860
atcttggatg ccaaagcgct cgaagatcaa gcaggaacca atcttgaaat cactataatc   4920
actctaaaga gaaatgaaaa gttcagagac attagaccac atatacctac tcaaatcact   4980
gagacaaatg atggagtctt gatcgtgaac actagcaagt accccaatat gtatgttcct   5040
gtcggtgctg tgactgaaca gggatatcta aatctcggtg ggcgccaaac tgctcgtact   5100
ctaatgtaca actttccaac cagagcagga cagtgtggtg gagtcatcac atgtactggg   5160
aaagtcatcg ggatgcatgt tggtgggaac ggttcacacg ggtttgcagc ggccctgaag   5220
cgatcatact tcactcagag tcaaggtgaa atccagtgga tgagaccttc gaaggaagtg   5280
ggatatccaa tcataaatgc cccgtccaaa accaagcttg aacccagtgc tttccactat   5340
gtgtttgaag ggggtgaagga accagcagtc ctcactaaaa acgatcccag gcttaagaca   5400
aactttgagg aggcaatttt ctccaagtac gtgggtaaca aaattactga agtggatgag   5460
cacatgaaag aggcagtaga ccactatgct ggccagctca tgtcactaga catcaacaca   5520
gaacaaatgt gcttggagga tgccatgtat ggcactgatg gtctagaagc acttgatttg   5580
tccaccagtg ctggctaccc ttatgtagca atgggaaaga agaagagaga tatcttgaac   5640
aaacaaacca gagacactaa ggaaatgcaa aaactgctcg acacatatgg aatcaacctc   5700
ccactggtga cttatgtaaa ggatgaactt agatccaaaa caaaggttga gcaggggaaa   5760
tccagattaa ttgaagcttc tagtttgaat gactcagtgg caatgagaat ggcttttggg   5820
aacctatatg ctgcttttca caaaaaccca ggagtgataa caggttcagc agtagggtgc   5880
gatccagatt tgttttggag caaaattccg gtattgatgg aagagaagct gtttgccttt   5940
gactacacag ggtatgatgc atctctcagc cctgcttggt tcgaggcact aaagatggtg   6000
cttgagaaaa tcggattcgg agacagagtt gactacatcg actacctaaa ccactcacac   6060
cacctgtaca agaataaaac atactgtgtc aagggcggta tgccatctgg ttgctcaggc   6120
acttcaattt ttaactcaat gattaacaac ttgattatca ggacactctt actgaaaacc   6180
tacaagggca tagatttaga ccacctaaaa atgattgcct atggtgatga tgtaattgct   6240
tcctaccccc atgaagttga cgctagtctc ctagcccaat caggaaaaga ctatggacta   6300
actatgactc cagctgacaa atcagctata tttgaaacag tcacatggga gaatgtaaca   6360
ttcttgaaga gattcttcag ggcagacgag aaatacccat ttcttattca tccagtaatg   6420
ccaatgaagg aaattcatga atcaattaga tggacaaaag atcctaggaa cactcaggat   6480
cacgttcgct ctctgtgcct attagcttgg cacaatggcg aagaagaata taacaaattc   6540
ctagctaaaa tcaggagtgt gccaattgga agagctttat tgctcccaga gtactcaaca   6600
ttgtaccgcc gttggcttga ctcattttag                                    6630
```

-continued

<210> SEQ ID NO 2
<211> LENGTH: 6630
<212> TYPE: DNA
<213> ORGANISM: Artificial Sequence
<220> FEATURE:
<223> OTHER INFORMATION: optimized STR

<400> SEQUENCE: 2

```
atgggagctc aggtatcttc tcaaaaagtt ggggcccatg agaactctaa cagggcgtac     60

ggggggtcga ccataaacta caccaccata aattattata gggactctgc ctcgaacgcg    120

gcctcgaaac aagacttctc gcaagacccg tccaagttca ccgagccgat aaaggacgtc    180

ctcataaaaa ccgcacccat gctcaactcg cccaacatag aggcctgcgg gtactcggac    240

agggtcctcc aactaaccct cggtaactcc accataacca cccaagaggc ggccaactct    300

gtcgtcgcct acgggcgttg gccggagtac ctccgcgact cggaggcgaa ccccgttgac    360

caaccgaccg agcccgacgt cgccgcctgc cgcttctaca cgctcgacac cgtttcgtgg    420

acgaaagagt cgcgtgggtg gtggtggaag ttgccggacg ccctcaggga catgggttta    480

ttcgggcaaa acatgtacta ccactacctc gggcgctccg ggtacaccgt tcacgtccaa    540

tgcaacgcgt ccaaattcca ccaaggggcc ctcggagtct tcgcggtccc cgagatgtgc    600

ctcgcgggcg actcgaacac caccaccatg cacacctcgt accaaaacgc gaacccgggg    660

gagaaaggtg ggaccttcac ggggacgttc accccggaca ataaccaaac ctctccggcg    720

cgtcgcttct gcccggttga ctacttactt ggtaacggga cgctacttgg gaacgcgttc    780

gttttcccgc accaaataat aaacctccgt accaacaact gcgccaccct cgtcttaccg    840

tacgttaact ccttatcgat agactcgatg gtcaagcaca acaactgggg tatagccata    900

ctacccttgg cgcccctaaa cttcgcctcg gagtcctccc ccgagatacc cataaccttg    960

accatagcgc cgatgtgctg cgagttcaac ggtctaagga acattaccct cccccgtcta   1020

caagggctcc cggtcatgaa cacaccgggg tcgaaccaat acctaaccgc cgacaacttc   1080

caatctccgt gcgcgctccc ggagttcgac gttacccccc cgatagacat accgggggag   1140

gtcaagaaca tgatggagtt ggccgagata gacaccatga taccgttcga cctatcggcc   1200

accaaaaaga acaccatgga gatgtaccgc gtccgtctat cggacaaacc ccataccgac   1260

gacccgatat tatgcctctc tttatcgccc gcctctgacc cgcgcttgtc tcacaccatg   1320

ctaggtgaga tactcaacta ctacacccac tgggccggtt ccctcaagtt cacgttcctc   1380

ttctgtggtt ttatgatggc caccgggaaa ctcttggttt cttacgcgcc gccgggtgcg   1440

gacccccccca agaagcgtaa ggaggcgatg ttgggtaccc atgttatatg ggacataggt   1500

ctccaatcct cttgtaccat ggtcgttccc tggatatcga acaccacgta ccgtcaaacc   1560

atagacgact cgttcaccga ggggggttac atatcggtct tctaccaaac caggatagtc   1620

gtcccgctat cgaccccgag agagatggac atactagggt tcgtttctgc gtgcaacgac   1680

ttctcggttc gtttgatgcg tgacaccacc catatagagc aaaaagcgct cgcccaaggg   1740

ctagggcaaa tgctagagtc gatgatagac aacaccgtcc gtgagacggt tggggcggcc   1800

acctcgaggg acgccttacc caacaccgag gcgtcgggtc ccacccactc caaggagata   1860

ccggccttaa ccgccgttga gaccggggcg accaaccccc tcgtcccgtc ggacaccgtt   1920

caaaccaggc acgtcgtcca acaccgctct cgctctgagt cgtcgataga gtcgttcttc   1980

gcgcgtgggg cctgcgttac tataatgacc gttgacaacc ctgcctccac caccaacaag   2040

gacaagctct tcgccgtttg gaagataacc tacaaagaca ccgtccaact acgtcgcaaa   2100
```

-continued

```
ttggagttct tcacctactc gaggttcgac atggagttaa ccttcgttgt caccgccaac   2160
ttcaccgaga ccaacaacgg gcacgcgcta aaccaagttt accaaataat gtacgtcccc   2220
cccggggccc ccgttccgga gaaatgggac gactacacct ggcaaacctc ttctaacccc   2280
tctatattct acacctacgg taccgccccc gcgcgtatat cggtcccgta cgtcgggata   2340
tcgaacgcgt actctcactt ctacgacggg ttctccaaag tccccctcaa ggaccaatcg   2400
gccgccctcg gggactcctt atacggggcc gcctcgctca acgacttcgg gatattggcc   2460
gtcagggtcg tcaacgacca caacccgacc aaggtcacct ccaaaataag ggtttacctc   2520
aaaccgaaac acataagggt ctggtgcccg cgtccaccgc gcgccgttgc gtactacggg   2580
ccgggtgttg actacaagga cgggacgcta accccgttat ccaccaagga cctcaccacc   2640
tacggtttcg gtcaccaaaa caaagcggtt tacaccgccg ggtacaaaat atgcaactac   2700
catttggcga cccaagacga cttgcaaaac gccgttaacg tcatgtggtc gagggactta   2760
ctagtcaccg agtctagggc gcaagggacc gactctatag cccgctgcaa ctgcaacgcc   2820
ggggtttact actgcgagtc gaggcgcaaa tactaccccg tctccttcgt cgggcccacg   2880
ttccaataca tggaggccaa caactactac cccgcccgct accaatccca catgttaata   2940
gggcacggtt tcgcctcgcc cggggactgc ggggggatat taaggtgcca ccacggggtt   3000
atagggataa taaccgccgg gggagagggg ttggtcgcct tctccgacat aagggacttg   3060
tacgcgtacg aggaggaggc gatggagcaa gggataacca actacataga gtctctaggg   3120
gcggccttcg gttcgggttt cacccaacaa ataagtgaca aaataaccga gttgacaaac   3180
atggttacct cgaccataac cgagaagctc ctaaagaact tgataaagat aatatcctct   3240
ctcgtcataa taacccgcaa ttacgaggac accaccaccg ttttagccac cctcgcgcta   3300
ctagggtgcg acgcctctcc ctggcaatgg ctaaggaaga aagcctgcga cgtcctcgag   3360
ataccgtacg tcattaagca aggggactcg tggttgaaga agttcaccga ggcctgcaac   3420
gccgccaagg gtctcgagtg ggtttctaac aaaatatcta aattcataga ctggttaaag   3480
gagaaaataa taccccaagc cagggacaag ttggagttcg tcaccaaact aaggcaactc   3540
gagatgctcg agaaccaaat atctaccata caccaatctt gcccgtcgca agagcaccaa   3600
gagatactct tcaacaacgt caggtggcta tccatacaat cgaagcgctt cgcgccgcta   3660
tacgccgtgg aggcgaaaag gatacaaaaa ctcgagcata ctattaacaa ctacatacag   3720
ttcaagagca aacaccgtat tgaaccagta tgtttgctag tacacgggtc gccgggtacc   3780
ggtaaatcgg tcgccaccaa cctcatagcc agggcgatag ccgagaggga gaacacgtcc   3840
acgtactcgc tcccgccgga cccctctcac ttcgacggtt acaaacaaca aggtgttgtt   3900
ataatggacg acctcaacca aaaccccgac ggggcggaca tgaagctctt ctgtcaaatg   3960
gtctctaccg ttgagttcat acccccgatg gcctccctcg aggagaaagg tatactcttc   4020
acctctaact acgtcctcgc ctccaccaac tcttcgagga tatccccgcc gaccgttgcc   4080
cactcggacg ccctagcgcg ccgtttcgcg ttcgacatgg acatacaagt catgaacgag   4140
tactcgaggg acgggaaatt gaacatggcg atggccaccg agatgtgtaa gaactgtcac   4200
caacccgcca acttcaagag gtgctgcccg ctagtttgcg ggaaggccat acaactaatg   4260
gacaaatcgt ccagggtcag gtactcgata gaccaaataa ccaccatgat aataaacgag   4320
aggaacagga ggtccaacat agggaactgt atggaggcct tgttccaagg tcccttacaa   4380
tacaaagact tgaagataga cataaagacg tcgccgccgc cggagtgcat aaacgacttg   4440
```

-continued

```
ttacaagccg tcgactccca agaggttagg gactactgtg agaagaaggg gtggatagtc   4500
aacataacct cgcaagtcca aaccgagcgc aacataaacc gcgccatgac catactccaa   4560
gcggttacca ccttcgcggc cgttgccggt gtcgtctacg tcatgtacaa actcttcgcc   4620
ggtcaccaag gtgcctacac cggcctaccc aacaaaaaac cgaacgttcc gaccataaga   4680
accgccaagg tccaagggcc cgggttcgac tacgccgttg ccatggccaa aaggaacata   4740
gtcaccgcca ccacctcgaa gggtgagttc accatgctag gtgtccacga caacgttgcc   4800
atactaccca cccacgcctc tccgggggag tcgatagtta tagacgggaa agaggttgag   4860
atattggacg cgaaagcgtt agaggaccaa gccggtacca acctagagat aaccataata   4920
accctcaaga ggaacgagaa gttcagggac ataaggcccc acataccgac ccaaataacc   4980
gagaccaacg acggagtctt gatcgtgaac actagcaagt accccaatat gtatgttcct   5040
gtcggtgctg tgactgaaca gggatatcta aatctcggtg ggcgccaaac cgcccgtacc   5100
ctcatgtaca acttccccac cagggccggt caatgcgggg gtgtcataac ctgcaccggg   5160
aaagtcatcg ggatgcatgt tggtgggaac ggttcacacg ggtttgcagc ggccctgaag   5220
cgatcatact tcacccaatc gcaaggggag atacaatgga tgaggccgtc gaaggaggtt   5280
ggttacccca taataaacgc gccgtccaaa accaagctag agccgtcggc cttccactac   5340
gttttcgagg gggttaagga gcccgccgtc ttaaccaaaa acgacccgcg cctaaagacc   5400
gatttcgagg aggccatatt ctccaagtac gttgggaaca aaataaccga ggttgacgag   5460
tatatgaaag aggccgtcga ccactacgcc gggcaattaa tgtctctcga cataaacacc   5520
gagcaaatgt gcttggagga cgcgatgtac gggaccgacg ggctcgaggc cctagacttg   5580
tccacctcgg ccgggtatcc gtacgtcgcc atgggtaaga agaagaggga tatattgaac   5640
aaacaaacca gggacaccaa ggagatgcaa aaactcttag acacctacgg tataaactta   5700
cccctcgtta cctacgtcaa ggacgagcta aggtccaaaa ccaaggtcga gcaagggaaa   5760
tccaggctaa tagaggcctc gtcgttgaac gactctgttg ccatgaggat ggccttcggg   5820
aacctctacg ccgccttcca caaaaacccc ggtgttataa ccgggtctgc cgtggggtgc   5880
gaccccgact tgttctggtc gaaaataccg gtcttgatgg aggagaagct cttcgccttc   5940
gactacaccg ggtacgacgc ctcgttatcg ccggcctggt tcgaggccct caagatggtt   6000
ctagagaaaa taggtttcgg tgacagggtc gactacatag actacctcaa ccactctcac   6060
cacctctaca agaacaaaac ctactgcgtc aaggggggga tgccctcggg atgctctggg   6120
acctctatat tcaactctat gataaacaac ttgataatac gcaccttact actcaaaacc   6180
tacaagggga tagacctaga ccacctcaaa atgatagcgt acggggacga cgtcatagcc   6240
tcctaccccc atgaagttga cgctagtctc ctagcccaat caggaaaaga ctatggacta   6300
actatgactc cagctgacaa atcagctaca tttgagaccg tcacctggga gaacgtcacc   6360
ttcttgaaga ggttcttccg cgccgacgag aaatacccct tcctaataca ccccgtcatg   6420
cccatgaagg agatacacga gtctataagg tggaccaaag acccgcgcaa cactcaggat   6480
cacgttcgct ctctgtgcct tttagcttgg cacaatggcg aagaagaata taacaaattc   6540
ctagctaaaa tcaggagtgt gccaattgga agagctttat tgctcccaga gtactcaaca   6600
ttgtaccgcc gttggcttga ctcattttag                                    6630
```